US010028999B2

(12) United States Patent
Chapman et al.

(10) Patent No.: US 10,028,999 B2
(45) Date of Patent: Jul. 24, 2018

(54) PAR-1 BASED THERAPEUTIC CONJUGATES AND USES THEREOF

(71) Applicant: TEL HASHOMER MEDICAL RESEARCH INFRASTRUCTURE AND SERVICES LTD., Ramat Gan (IL)

(72) Inventors: Joab Chapman, Kiryat Ono (IL); Efrat Shavit-Stein, Tel Aviv (IL)

(73) Assignee: TEL HASHOMER MEDICAL RESEARCH INFRASTRUCTURE AND SERVICES LTD., Ramat Gan (IL)

(*) Notice: Subject to any disclaimer, the term of this patent is extended or adjusted under 35 U.S.C. 154(b) by 0 days.

(21) Appl. No.: 15/309,195

(22) PCT Filed: May 11, 2015

(86) PCT No.: PCT/IL2015/050488
§ 371 (c)(1),
(2) Date: Nov. 6, 2016

(87) PCT Pub. No.: WO2015/173802
PCT Pub. Date: Nov. 19, 2015

(65) Prior Publication Data
US 2017/0072014 A1 Mar. 16, 2017

Related U.S. Application Data

(60) Provisional application No. 61/991,532, filed on May 11, 2014, provisional application No. 62/137,846, filed on Mar. 25, 2015.

(51) Int. Cl.
A61K 38/57 (2006.01)
A61K 38/17 (2006.01)
C07K 14/72 (2006.01)
C07K 5/083 (2006.01)
C07K 5/093 (2006.01)
C07K 5/103 (2006.01)
C07K 5/117 (2006.01)
A61K 45/06 (2006.01)
A61K 38/00 (2006.01)

(52) U.S. Cl.
CPC .......... *A61K 38/1796* (2013.01); *A61K 38/57* (2013.01); *A61K 45/06* (2013.01); *C07K 5/0806* (2013.01); *C07K 5/0819* (2013.01); *C07K 5/101* (2013.01); *C07K 5/1024* (2013.01); *C07K 14/723* (2013.01); *A61K 38/00* (2013.01)

(58) Field of Classification Search
None
See application file for complete search history.

(56) References Cited

U.S. PATENT DOCUMENTS

| 4,161,522 A * | 7/1979 | Hamburger .......... C07K 5/0819 514/21.7 |
| 4,966,848 A * | 10/1990 | Smith .................. C12N 9/1029 435/193 |
| 5,223,421 A * | 6/1993 | Smith .................. C12N 9/1029 435/193 |
| 5,837,218 A * | 11/1998 | Peers .................. A61K 51/088 424/1.65 |
| 7,842,716 B2 | 11/2010 | Serebruany |
| 8,232,295 B2 | 7/2012 | Serebruany |
| 9,180,163 B2 * | 11/2015 | Tsopanoglou ......... A61K 38/10 |
| 2004/0092535 A1 | 5/2004 | Barsanti |
| 2007/0142272 A1 | 6/2007 | Zlokovic |
| 2009/0176803 A1 | 7/2009 | Perez |
| 2009/0281100 A1 | 11/2009 | Barsanti |
| 2012/0232097 A1 | 9/2012 | Perez |

FOREIGN PATENT DOCUMENTS

| WO | 02071847 | 9/2002 |
| WO | 2013070256 | 5/2013 |
| WO | 2013173676 | 11/2013 |

OTHER PUBLICATIONS

Nikos Zania, et al Panagiota et., al Journal of Pharmacology and Experimental Therapeutics Feb. 1, 2009, 328 (2) 378-389.*
McRedmond JP et al, Streptokinase-induced platelet activation involves antistreptokinase antibodies and cleavage of protease-activated receptor-1Blood. Feb. 15, 2000;95(4):1301-8 (Year: 2000).*
Mihara et al., (2013) Neutrophil elastase and proteinase-3 trigger G protein-biased signaling through proteinase-activated receptor-1 (PAR1). Journal of Biological Chemistry, 288(46), 32979-32990.
Shavit et al., (2008) Thrombin receptor PAR-1 on myelin at the node of Ranvier: a new anatomy and physiology of conduction block. Brain, 131(4), 1113-1122.
Shavit et al., (2011) Anatomical localization of protease-activated receptor-1 and protease-mediated neuroglilal crosstalk on peri-synaptic astrocytic endfeet. Journal of neurochemistry, 119(3), 460-473.
International Search Report for PCT/IL2015/050488 Completed Aug. 26, 2015; dated Aug. 27, 2015 6 Pages.

(Continued)

*Primary Examiner* — Thomas S Heard
(74) *Attorney, Agent, or Firm* — Roy Gross; The Roy Gross Law Firm, LLC

(57) ABSTRACT

The present invention is directed to a peptide conjugate comprising an alpha-amino protecting moiety, a peptide comprising the amino acid sequence at least 3 amino-acid long derived from the C'-terminus of PAR-1, or an active variant thereof and a protease-disabling moiety. The present invention is further directed to pharmaceutical compositions comprising the peptide conjugate and use thereof for treating diseases and disorder associated with excessive PAR-1 activity.

15 Claims, 26 Drawing Sheets

(56) References Cited

OTHER PUBLICATIONS

Written Opiniont for PCT/IL2015/050488 Completed Aug. 26, 2015 7 Pages.

* cited by examiner

SEQUENCE LISTING

```
<160> NUMBER OF SEQ ID NOS: 19

<210> SEQ ID NO 1
<211> LENGTH: 4
<212> TYPE: PRT
<213> ORGANISM: Artificial sequence
<220> FEATURE:
<223> OTHER INFORMATION: Peptide

<400> SEQUENCE: 1

Leu Asp Pro Arg
1

<210> SEQ ID NO 2
<211> LENGTH: 5
<212> TYPE: PRT
<213> ORGANISM: Artificial sequence
<220> FEATURE:
<223> OTHER INFORMATION: Peptide

<400> SEQUENCE: 2

Thr Leu Asp Pro Arg
1               5

<210> SEQ ID NO 3
<211> LENGTH: 6
<212> TYPE: PRT
<213> ORGANISM: Artificial sequence
<220> FEATURE:
<223> OTHER INFORMATION: Peptide

<400> SEQUENCE: 3

Ala Thr Leu Asp Pro Arg
1               5

<210> SEQ ID NO 4
```

```
<211> LENGTH: 7
<212> TYPE: PRT
<213> ORGANISM: Artificial sequence
<220> FEATURE:
<223> OTHER INFORMATION: Peptide

<400> SEQUENCE: 4

Asn Ala Thr Leu Asp Pro Arg
1               5

<210> SEQ ID NO 5
<211> LENGTH: 8
<212> TYPE: PRT
<213> ORGANISM: Artificial sequence
<220> FEATURE:
<223> OTHER INFORMATION: Peptide

<400> SEQUENCE: 5

Thr Asn Ala Thr Leu Asp Pro Arg
1               5

<210> SEQ ID NO 6
<211> LENGTH: 9
<212> TYPE: PRT
<213> ORGANISM: Artificial sequence
<220> FEATURE:
<223> OTHER INFORMATION: Peptide

<400> SEQUENCE: 6

Ala Thr Asn Ala Thr Leu Asp Pro Arg
1               5

<210> SEQ ID NO 7
<211> LENGTH: 10
<212> TYPE: PRT
<213> ORGANISM: Artificial sequence
<220> FEATURE:
<223> OTHER INFORMATION: Peptide

<400> SEQUENCE: 7

Lys Ala Thr Asn Ala Thr Leu Asp Pro Arg
1               5                   10

<210> SEQ ID NO 8
<211> LENGTH: 11
<212> TYPE: PRT
<213> ORGANISM: Artificial sequence
<220> FEATURE:
<223> OTHER INFORMATION: Peptide

<400> SEQUENCE: 8

Ser Lys Ala Thr Asn Ala Thr Leu Asp Pro Arg
1               5                   10

<210> SEQ ID NO 9
<211> LENGTH: 12
<212> TYPE: PRT
<213> ORGANISM: Artificial sequence
<220> FEATURE:
<223> OTHER INFORMATION: Peptide

<400> SEQUENCE: 9

Glu Ser Lys Ala Thr Asn Ala Thr Leu Asp Pro Arg
1               5                   10

<210> SEQ ID NO 10
<211> LENGTH: 13
```

```
<212> TYPE: PRT
<213> ORGANISM: Artificial sequence
<220> FEATURE:
<223> OTHER INFORMATION: Peptide

<400> SEQUENCE: 10

Pro Glu Ser Lys Ala Thr Asn Ala Thr Leu Asp Pro Arg
1               5                   10

<210> SEQ ID NO 11
<211> LENGTH: 14
<212> TYPE: PRT
<213> ORGANISM: Artificial sequence
<220> FEATURE:
<223> OTHER INFORMATION: Peptide

<400> SEQUENCE: 11

Arg Pro Glu Ser Lys Ala Thr Asn Ala Thr Leu Asp Pro Arg
1               5                   10

<210> SEQ ID NO 12
<211> LENGTH: 15
<212> TYPE: PRT
<213> ORGANISM: Artificial sequence
<220> FEATURE:
<223> OTHER INFORMATION: Peptide

<400> SEQUENCE: 12

Arg Arg Pro Glu Ser Lys Ala Thr Asn Ala Thr Leu Asp Pro Arg
1               5                   10                  15

<210> SEQ ID NO 13
<211> LENGTH: 16
<212> TYPE: PRT
<213> ORGANISM: Artificial sequence
<220> FEATURE:
<223> OTHER INFORMATION: Peptide

<400> SEQUENCE: 13

Ala Arg Arg Pro Glu Ser Lys Ala Thr Asn Ala Thr Leu Asp Pro Arg
1               5                   10                  15

<210> SEQ ID NO 14
<211> LENGTH: 17
<212> TYPE: PRT
<213> ORGANISM: Artificial sequence
<220> FEATURE:
<223> OTHER INFORMATION: Peptide

<400> SEQUENCE: 14

Arg Ala Arg Arg Pro Glu Ser Lys Ala Thr Asn Ala Thr Leu Asp Pro
1               5                   10                  15

Arg

<210> SEQ ID NO 15
<211> LENGTH: 18
<212> TYPE: PRT
<213> ORGANISM: Artificial sequence
<220> FEATURE:
<223> OTHER INFORMATION: Peptide

<400> SEQUENCE: 15

Thr Arg Ala Arg Arg Pro Glu Ser Lys Ala Thr Asn Ala Thr Leu Asp
1               5                   10                  15

Pro Arg
```

```
<210> SEQ ID NO 16
<211> LENGTH: 19
<212> TYPE: PRT
<213> ORGANISM: Artificial sequence
<220> FEATURE:
<223> OTHER INFORMATION: Peptide

<400> SEQUENCE: 16

Arg Thr Arg Ala Arg Arg Pro Glu Ser Lys Ala Thr Asn Ala Thr Leu
1               5                   10                  15

Asp Pro Arg

<210> SEQ ID NO 17
<211> LENGTH: 20
<212> TYPE: PRT
<213> ORGANISM: Artificial sequence
<220> FEATURE:
<223> OTHER INFORMATION: Peptide

<400> SEQUENCE: 17

Ala Arg Thr Arg Ala Arg Arg Pro Glu Ser Lys Ala Thr Asn Ala Thr
1               5                   10                  15

Leu Asp Pro Arg
            20

<210> SEQ ID NO 18
<211> LENGTH: 18
<212> TYPE: PRT
<213> ORGANISM: Artificial sequence
<220> FEATURE:
<223> OTHER INFORMATION: Peptide

<400> SEQUENCE: 18

Leu Asp Pro Arg Ser Phe Leu Leu Arg Asn Pro Asn Asp Lys Tyr Glu
1               5                   10                  15

Pro Phe

<210> SEQ ID NO 19
<211> LENGTH: 5
<212> TYPE: PRT
<213> ORGANISM: Artificial sequence
<220> FEATURE:
<223> OTHER INFORMATION: Peptide

<400> SEQUENCE: 19

Lys Tyr Glu Pro Phe
1               5
```

PAR-1 BASED THERAPEUTIC CONJUGATES AND USES THEREOF

RELATED APPLICATIONS

This application is a 35 U.S.C. § 371 national phase application of PCT/IL2015/050488, filed May 11, 2015, which claims priority to US 61/991,532 filed on May 11, 2014 and US 62/137,846 filed on Mar. 25, 2015. All applications are incorporated herein by reference as if fully set forth.

FIELD OF THE INVENTION

The present invention is directed to a peptide conjugate comprising an alpha-amino protecting moiety, a peptide comprising the amino acid sequence at least 3 amino-acid long derived from the C'-terminus of PAR-1, or an active variant thereof and a protease-disabling moiety. The present invention is further directed to pharmaceutical compositions comprising the peptide conjugate and use thereof for treating diseases and disorder associated with excessive PAR-1 activity.

BACKGROUND OF THE INVENTION

Protease activated receptors (PARs) are a family of four G protein coupled receptors numbered PAR-1 to PAR-4. Since its discovery in the early 90's, PAR-1 has been found in many tissues including the brain where it is found on several cell types including neurons, astrocytes and microglia. The first functions of PAR-1 described in neurons and glia involved cell survival and cell death. This dual effect is concentration dependent where at high levels of PAR-1 activation deleterious effects are seen and at lower levels protective effects are seen. PAR-1 carries all determinants required for thrombin recognition.

Many neurological diseases are known to be associated with increased inflammation and over activation of protease activated receptors (PARs) by protein factors of the coagulation cascade. This include, neuropathy which is commonly caused by diabetes mellitus, occurring in 60% of all diabetic patients.

Many studies have suggested that thrombin plays a role in angiogenesis and its inhibition reduces edema. Glioblastoma multiform, (GBM) is a rapidly growing brain tumor resulting in high mortality within month. Several processes characterize GBM including increased angiogenesis, edema formation and enhanced tumor cell proliferation.

US 2009/0281100 and US 2004/0092535 disclose a method of inhibiting a serine/threonine kinase using benzimidazole quinolinones, wherein the serine/threonine kinase is PAR-1, for treating diabetes, noninsulin dependent diabetes mellitus, Alzheimer's disease, bipolar disorder, cancer, autoimmune diseases and organ transplant rejection.

US 2012/0232097 and US 2009/0176803 disclose cinnamoyl-piperazine derivatives as PAR-1 antagonists and uses thereof for treating and/or preventive arterial/venous thrombosis, acute coronary syndromes, restenosis, stable angina, heart rhythm disorders, myocardial infarction, hypertension, heart failure, stroke, inflammatory disorders, pulmonary diseases, gastrointestinal diseases, fibrosis development in chronic liver disease patients, cancer and skin diseases.

U.S. Pat. Nos. 8,232,295 and 7,842,716 disclose methods for treating and/or preventing vascular events by inhibiting PAR-1 and/or PAR-4 using statins.

US 2007/0142272 discloses use of an activated protein C (APC), prodrug and/or a variant thereof as agonist of PAR-1 and/or PAR-3 and/or endothelial protein C receptor (EPCR) for providing neuroprotection, treating neurodegenerative disease and improving stress or injury.

Despite efforts made in the field, there remains an unmet need in the art for potent inhibitors that inhibit or prevent over activation of PARs, especially, PAR-1.

SUMMARY OF THE INVENTION

The present invention provides novel peptide conjugates capable of targeting increased protease activity associated with diseases and disorders. The peptide conjugates of the invention are adapted to specifically protect PAR receptors from being over-activated. Surprisingly, the peptide conjugates of the invention were shown to inhibit thrombin activity, reduce thrombin-like activity generated by glioma-cells, inhibit proliferation of glioma cells, induce reduction in glioblastoma multiform (GBM) tumors in vivo and reduced formation of edema associated with GBM. Advantageously, the peptide conjugates exert the aforementioned therapeutic activities at significantly low concentrations, within the range of nanomolars in vitro and micromolars in vivo, while known PAR1 inhibitors require much higher concentrations in order to exert an inhibitory activity. Moreover, the activity of the peptide conjugate is performed without effecting coagulation. The remarkable efficacy at nanomolar concentrations suggests that the conjugates provide reduced toxicity and reduced occurrence of side effects, particularly, undesired internal bleeding.

There is provided a peptide conjugate comprising an alpha-amino protecting moiety, a peptide comprising the amino acid sequence at least 3 amino-acid long derived from the C'-terminus of PAR-1 as set forth in SEQ ID NO: 17, or an active variant thereof and a protease-disabling moiety.

In some embodiments, the alpha-amino protecting moiety may be bound to the N'-terminus amino acid sequence of the peptide directly or via a linker.

In some embodiments, the protease-disabling moiety may be bound to the C'-terminus amino acid sequence of the peptide directly or via a linker.

In some embodiments, the alpha-amino protecting moiety may be selected from tosyl and tert-Butyloxycarbonyl.

In some embodiments, the alpha-amino protecting moiety may be tosyl or derivatives thereof.

In some embodiments, the peptide comprises the amino acid sequence Asp-Pro-Arg.

In some embodiments, the peptide comprises an amino acid sequence as set forth in any one of SEQ ID NO:1 to SEQ ID NO:17 and Asp-Pro-Arg, or an active variant thereof.

In some embodiments, the peptide comprises the amino acid set forth in SEQ ID NO:3, or an active variant thereof.

In some embodiments, the peptide comprises the amino acid set forth in SEQ ID NO:4, or an active variant thereof.

In some embodiments, the peptide moiety may consist of an amino acid sequence selected from the group consisting of Asp-Pro-Arg and SEQ ID NO: 1 to SEQ ID NO:17.

In some embodiments, the linker may be a peptide linker or an oligonucleotide linker.

In some embodiments, the protease-disabling moiety may be a substituted acetyl.

In some embodiments, the protease-disabling moiety may be selected from the group consisting of sulfonylfluorides, chloromethylketones, esters, boronic acids, aldehydes, arylketones, trifluoromethylketones, ketocarboxylic acids and combinations thereof.

In some embodiments, the protease-disabling moiety may be chloromethylketone and derivatives thereof.

In some embodiments, the alpha-amino protecting moiety may be tosyl or a derivative thereof, the peptide comprises the amino acid sequence Asp-Pro-Arg or an active variant thereof and the protease-disabling moiety may be a haloacetyl.

There is provided a pharmaceutical composition comprising a peptide conjugate and a pharmaceutically acceptable carrier, said peptide conjugate comprising an alpha-amino protecting moiety, a peptide comprising the amino acid sequence at least 3 amino-acid long derived from the C'-terminus of PAR-1 as set forth in SEQ ID NO: 17, or an active variant thereof and a protease-disabling moiety.

In some embodiments, the pharmaceutical composition may further include trichloroacetate.

In some embodiments, the pharmaceutical composition may further include a PAR-1 antagonist.

In some embodiments, the PAR-1 antagonist may be SCH79797 (N3-Cyclopropyl-7-[[4-(1-methylethyl)phenyl]methyl]-7H-pyrrolo[3,2-f]quinazoline-1,3-diamine dihydrochloride).

There is provided use of a pharmaceutical composition comprising a peptide conjugate and a pharmaceutically acceptable carrier, said peptide conjugate comprising an alpha-amino protecting moiety, a peptide comprising the amino acid sequence at least 3 amino-acid long derived from the C'-terminus of PAR-1 as set forth in SEQ ID NO: 17, or an active variant thereof and a protease-disabling moiety, for the treatment of a disease or disorder associated with excessive protease receptor activity.

In some embodiments, the protease receptor may be PAR-1.

In some embodiments, the disease or disorder may be selected from the group consisting of neuroinflammation, neuroinflammatory diseases or disorders, neurodegenerative disease or disorder, neuropathy and diabetes-related neuropathy.

In some embodiments, the use may be for the treatment of a tumor associated with said disease or disorder.

In some embodiments, the diseases or disorders may be selected from the group consisting of: glioma, astrocytomas, cancer, solid tumor, brain tumor, glioblastoma, oligodendroglioma, ependymoma, mixed gliomas glioblastoma multiforme, neuropathy, diabetic peripheral neuropathy, Guillain-Barré syndrome, amyotrophic lateral sclerosis, acute inflammatory demyelinating polyneuropathy, acute disseminated encephalomyelitis, optic neuritis, transverse myelitis, neuromyelitis optica, Alzheimer's disease, Huntington's disease, amyotrophic lateral sclerosis, epilepsy, multiple sclerosis and Parkinson's disease.

In some embodiments, the treatment may include any one or more of inhibition of the progression of said disease or disorder, attenuation of the progression of said disease or disorder or prevention deterioration of said disease or disorder.

There is provided a method of treating a disease or disorder associated with excessive protease receptor activity in a patient in need of such treatment, the method comprises the step of administering to said patient a therapeutically effective amount of a pharmaceutical composition comprising a peptide conjugate and a pharmaceutically acceptable carrier, said peptide conjugate comprising an alpha-amino protecting moiety, a peptide comprising the amino acid sequence at least 3 amino-acid long derived from the C'-terminus of PAR-1 as set forth in SEQ ID NO: 17, or an active variant thereof and a protease-disabling moiety.

In some embodiments, the pharmaceutical composition may be administered topically, intraperitoneally, systemically or intra-cranially.

In some embodiments, the treating may include any one or more of inhibiting the progression of said disease or disorder, attenuating the progression of said disease or disorder or preventing deterioration of said disease or disorder.

In some embodiments, the subject in need thereof may be a subject afflicted with said disease or disorder or a subject susceptible to said disease or disorder.

In some embodiments, the method may further comprise administering a second therapeutic agent in combination with said peptide conjugate.

In some embodiments, the second therapeutic agent may be a PAR-1 antagonist.

There is provided use of a pharmaceutical composition comprising a peptide conjugate and a pharmaceutically acceptable carrier, said peptide conjugate comprising an alpha-amino protecting moiety, a peptide comprising the amino acid sequence at least 3 amino-acid long derived from the C'-terminus of PAR-1 as set forth in SEQ ID NO: 17, or an active variant thereof and a protease-disabling moiety, for inducing a reduction in thrombin activity.

There is provided a kit for treating a disease or disorder associated with excessive protease receptor activity in a patient in need of such treatment, the kit comprises at least one container comprising a therapeutically effective amount of a pharmaceutical composition comprising a peptide conjugate and a pharmaceutically acceptable carrier, said peptide conjugate comprising an alpha-amino protecting moiety, a peptide comprising the amino acid sequence at least 3 amino-acid long derived from the C'-terminus of PAR-1 as set forth in SEQ ID NO: 17, or an active variant thereof and a protease-disabling moiety.

In some embodiments, the kit may further comprise at least one second container that includes a second therapeutic agent. In some embodiments, the second therapeutic agent may be a PAR-1 antagonist.

In some embodiments, the kit may further include instructions for use of the pharmaceutical composition for the treatment of the disease or disorder. In some embodiments, the instructions for use may include instructions for using the pharmaceutical composition in the at least one first container in combination with the pharmaceutical composition in the at least one second container. In some embodiments, the instructions may further recite a web site address providing further information, and troubleshooting among other services. In some embodiments, the instructions may be on paper form such as a package insert or label.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1A:
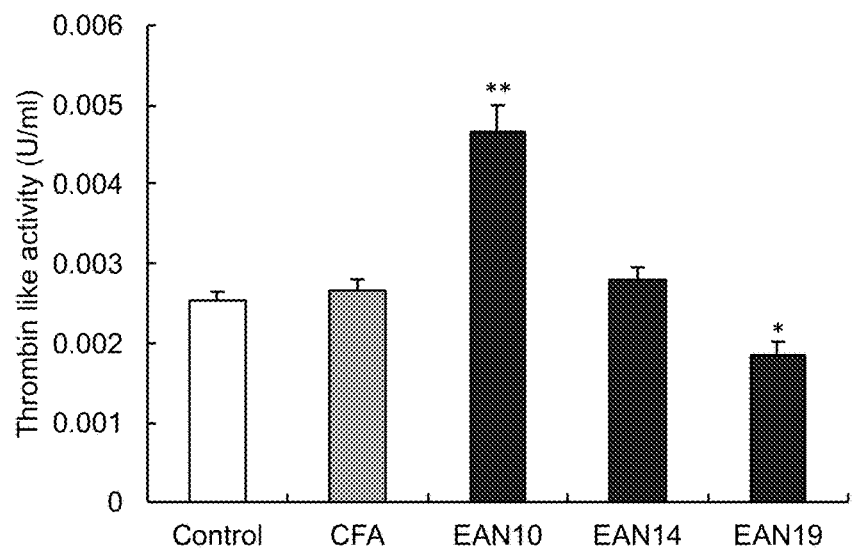
FIG. 1 shows mean thrombin-like activity (U/ml±SEM) in sciatic nerves of (A) EAN rats at day of induction and at 10, 14 and 19 days post induction (EAN 10, n=10; EAN14, n=10; EAN19, n=10, respectively) vs. control rats (n=10) and CFA (complete Freund's adjuvant) mice; and in (B) STZ rats (n=15) vs. control rats (n=12) (**=p<0.01; *=p<0.005).

The present invention provides novel peptide conjugates that target an increased protease activity associated with diseases and disorders by specifically protecting PAR receptors from being over-activated.

It has long been recognized that in PAR-1 (NP_001983.2) the extracellular fragment (amino-terminal exodomain) carries all determinants for thrombin recognition. In some embodiments, the sequence of said amino-terminal exodomain is as follows: $^{38}$LDPRSFLLRNPNDKYEPF$^{55}$ (SEQ ID NO: 18). This peptide sequence is bridging thrombin active site and exosite I. Furthermore, the sequence $^{38}$LDPR$^{41}$ (also termed LDPR; SEQ ID NO: 1), is contacting the thrombin active site and the acidic hirudin-like motif, $^{51}$KYEPF$^{55}$ (SEQ ID NO: 19), thereby engaging thrombin exosite I. Although the highest binding affinity and maximal proximity was found between $^{38}$LDPR$^{41}$ (P1 to P4; (SEQ ID NO: 1) and the active site of thrombin, a 3D modeling of PAR-1 N-terminal peptide and thrombin reveals contacts (with lower strength) up to amino acid at position 20 (P20). PAR-1 activation requires specific binding of thrombin and similar proteases to a binding site on the receptor, which is just preceding the cleavage site. The binding site on the receptor PAR-1 comprises the amino acid sequence PESKATNATLDPR (SEQ ID NO: 10) that is significantly different from the equivalent sequences in PAR-2, 3 and 4. As exemplified in Table 2, hereinbelow, there is a high degree of homology between the human, mouse, rat and bovine PAR-1 in positions P1 to P7, wherein the highest homology is at P1-P2 and P5-P7.

In the nervous system a major factor is played by the activation of PARs on glia cells. In the peripheral nervous system (PNS), PAR-1 is localized to the non-compacted myelin of Schwann cells at the node of Ranvier, and in the neuromuscular junction it is localized to the peri-synaptic glia and the post-synaptic muscle. The inventors of the present invention were the first to show a functional role for PAR-1 activation on the glia component of the node of Ranvier in the PNS where activation of the receptor caused nerve conduction block (Shavit et al., Brain, 2008, vol. 131(Pt 4): p. 1113-1122). In the central nervous system (CNS) PAR-1 was found on neurons and glia. It was suggested that PAR-1 is localized to a specific astrocyte structure at the synapse, and the inventors of the present invention have confirmed this location by high resolution methods such as confocal and electron microscopy (Shavit et al., J Neurochem. 119(3): p. 460-473). PAR-1 activation was shown to hold a physiological role at the CNS synapse where its activation modulates synaptic transmission by causing long-term potentiation (LTP) and seizure-like activity and potentiates the synaptic N-methyl-D-aspartate (NMDA) receptor. It is interesting to note therefore that PAR-1 is a marker of glial structures adjacent to the most physiologically active parts of the nervous system, the synapse and the node of Ranvier.

Thus, there is provided a peptide conjugate comprising a protecting moiety, a peptide comprising the amino acid sequence DPR (also termed Asp-Pro-Arg) or an active variant thereof and a thrombin-disabling moiety.

In some embodiments, the peptide conjugate may comprise the following structure: PRO-PEP-DIS, wherein PRO is a protecting moiety, such as, an alpha-amino protecting moiety; PEP is a peptide moiety comprising the amino acid sequences DPR or amino acid sequences comprising same, as set forth in SEQ ID NO:2 to SEQ ID NO:17, or an active variant thereof; and DIS may be a protease-disabling moiety, wherein PRO may be bound to the N'-terminus amino acid of PEP directly or via a linker, and wherein DIS may be bound to the C'-terminus amino-acid of PEP directly or via a linker. Each possibility represents a separate embodiment of the present invention.

The terms "peptide moiety" and "PEP" are interchangeable and refer to a peptide moiety derived from the PAR-1, including, but not limited to, the C'-terminus of PAR-1 (SEQ ID NO: 17).

In some embodiments, the peptide moiety may have an amino-acid sequence at least 3 amino acid long derived from the C'-terminus of PAR-1.

In some embodiments, the peptide moiety may have an amino-acid sequence at least 3 amino-acid long and at most 7 amino-acid long, derived from the C'-terminus of PAR-1.

In some embodiments, the peptide moiety may have an amino-acid sequence of at least 3 amino-acid long and at most 7 amino-acid long derived from the C'-terminus of PAR-1 starting from Arginine at position 20 and continuing towards the N'-terminus.

In some embodiments, the amino-acid sequences of DPR and SEQ ID NO: 1 to SEQ ID NO:17 are fragments of the PAR-1 receptor, to which thrombin binds and the peptide conjugates of the present invention comprise such sequence as decoy for thrombin i.e. to enable their specific binding to thrombin.

In some embodiments, the peptide moiety comprises an amino-acid sequence selected from the group consisting of DPR, LDPR (SEQ ID NO: 1), TLDPR (SEQ ID NO: 2), ATLDPR (SEQ ID NO: 3), NATLDPR (SEQ ID NO: 4), TNATLDPR (SEQ ID NO: 5), ATNATLDPR (SEQ ID NO: 6), KATNATLDPR (SEQ ID NO: 7), SKATNATLDPR (SEQ ID NO: 8), ESKATNATLDPR (SEQ ID NO: 9), PESKATNATLDPR (SEQ ID NO: 10), RPESKATNATLDPR (SEQ ID NO: 11), RRPESKATNATLDPR (SEQ ID NO: 12), ARRPESKATNATLDPR (SEQ ID NO: 13), RARRPESKATNATLDPR (SEQ ID NO: 14), TRARRPESKATNATLDPR (SEQ ID NO: 15), RTRARRPESKATNATLDPR (SEQ ID NO: 16) and ARTRARRPESKATNATLDPR (SEQ ID NO: 17). Each possibility represents a separate embodiment of the present invention.

In some embodiments, the peptide moiety may consist of Asp-Pro-Arg (DPR). In some embodiments, the peptide moiety may consist of SEQ ID NO: 1. In some embodiments, the peptide moiety may consist of SEQ ID NO: 2. In some embodiments, the peptide moiety may consist of SEQ ID NO: 3. In some embodiments, the peptide moiety may consist of SEQ ID NO: 4. In some embodiments, the peptide moiety may consist of SEQ ID NO: 5. In some embodiments, the peptide moiety may consist of SEQ ID NO: 6. In some embodiments, the peptide moiety may consist of SEQ ID NO: 7. In some embodiments, the peptide moiety may consist of SEQ ID NO: 8. In some embodiments, the peptide moiety may consist of SEQ ID NO: 9. In some embodiments, the peptide moiety may consist of SEQ ID NO: 10. In some embodiments, the peptide moiety may consist of SEQ ID NO: 11. In some embodiments, the peptide moiety may consist of SEQ ID NO: 12. In some embodiments, the peptide moiety may consist of SEQ ID NO: 13. In some embodiments, the peptide moiety may consist of SEQ ID NO: 14. In some embodiments, the peptide moiety may consist of SEQ ID NO: 15. In some embodiments, the peptide moiety may consist of SEQ ID NO: 16. In some embodiments, the peptide moiety may consist of SEQ ID NO: 17.

In some embodiments, the peptide moiety may comprise an amino-acid sequence Asp-Pro-Arg or an active variant thereof. In some embodiments, the peptide moiety may comprise an amino-acid sequence set forth in SEQ ID NO: 1 or an active variant thereof. In some embodiments, the peptide moiety may comprise an amino-acid sequence set forth in SEQ ID NO: 2 or an active variant thereof. In some embodiments, the peptide moiety may comprise an amino-acid sequence set forth in SEQ ID NO: 3 or an active variant thereof. In some embodiments, the peptide moiety may comprise an amino-acid sequence set forth in SEQ ID NO: 4 or an active variant thereof. In some embodiments, the peptide moiety may comprise an amino-acid sequence set forth in SEQ ID NO: 5 or an active variant thereof. In some embodiments, the peptide moiety may comprise an amino-acid sequence set forth in SEQ ID NO: 6 or an active variant thereof. In some embodiments, the peptide moiety may comprise an amino-acid sequence set forth in SEQ ID NO: 7 or an active variant thereof. In some embodiments, the peptide moiety may comprise an amino-acid sequence set forth in SEQ ID NO: 8 or an active variant thereof. In some embodiments, the peptide moiety may comprise an amino-acid sequence set forth in SEQ ID NO: 9 or an active variant thereof. In some embodiments, the peptide moiety may comprise an amino-acid sequence set forth in SEQ ID NO: 10 or an active variant thereof. In some embodiments, the peptide moiety may comprise an amino-acid sequence set forth in SEQ ID NO: 11 or an active variant thereof. In some embodiments, the peptide moiety may comprise an amino-acid sequence set forth in SEQ ID NO: 12 or an active variant thereof. In some embodiments, the peptide moiety may comprise an amino-acid sequence set forth in SEQ ID NO: 13 or an active variant thereof. In some embodiments, the peptide moiety may comprise an amino-acid sequence set forth in SEQ ID NO: 14 or an active variant thereof. In some embodiments, the peptide moiety may comprise an amino-acid sequence set forth in SEQ ID NO: 15 or an active variant thereof. In some embodiments, the peptide moiety may comprise an amino-acid sequence set forth in SEQ ID NO: 16 or an active variant thereof. In some embodiments, the peptide moiety may comprise an amino-acid sequence set forth in SEQ ID NO: 17 or an active variant thereof.

The terms "active variant", "analogue" and "variant" as used herein are interchangeable and refer to any peptide moiety derived from a peptide sequence as set forth in DPR and any one of SEQ ID NO:1 to SEQ ID NO:17 by at least one amino-acid substitution, that retains at least 70%, optionally, at least 80% or at least 90% or at least 95%, of the biological activity of the sequence from which it was derived, or to which it is most similar to. These terms also encompass peptides comprising regions having substantial similarity to the peptide moiety, such as structural variants.

The term "substantial similarity" means that two peptide sequences, when optimally aligned, share at least 50 percent sequence identity, at least 60 percent sequence identity, at least 70 percent sequence identity, at least 80 percent sequence identity, at least 90 percent sequence identity, or at least 95 percent sequence identity or more (e.g., 99 percent sequence identity). Typically, residue positions, which are not identical, differ by conservative amino acid substitutions.

In some embodiments, one or more of the peptide moieties may correspond to variants of the amino-acid sequence DPR or the amino acid sequences set forth in SEQ ID NO:1 to SEQ ID NO:17. Each possibility represents a separate embodiment of the present invention.

In some embodiments, said variants may comprise conservative substitutions relative to the amino acid sequence of the peptide moiety corresponding thereto.

Examples of conservative substitutions as considered in the present invention are the substitution of any positive-charge amino-acid (Arg, His, Lys) with any other positive-charge amino-acid; the substitution of any negative-charge amino-acid (Asp, Glu) with any other negative-charge amino-acid; the substitution of any polar-uncharged amino-acid (Ser, Thr, Asn, Gln) with any other polar-uncharged amino-acid; or the substitution of any hydrophobic amino-acid (Ala, Ile, Leu, Met, Phe, Trp, Tyr, Val) with any other hydrophobic amino-acid.

Thus, in some embodiments, active variant may comprise Arg/His/Lys substitution; Asp/Glu substitution; Ser/Thr/Asn/Gln substitution; Ala/Ile/Leu/Met/Phe/Trp/Tyr/Val substitution; or any combination of the above. Each possibility represents a separate embodiment of the present invention.

In some embodiments, the peptide may be selected from the amino-acid sequences DPR and those set forth in SEQ ID NOs: 1 to 17, wherein at least on proline is substituted with a positive-charge amino acid. In other embodiments, the peptide is selected from DPR and SEQ ID NOs: 1 to 17, wherein at least on proline is substituted with lysine. Without being bound by any theory of mechanism, the peptide is substituted in order to obtain improved specificity to thrombin and potentially other coagulation factors, improved penetration into the brain and prolonged half-life of the conjugate.

Residue positions, which are not identical, may also be composed of peptide analogs, including unnatural amino acids or derivatives of such. Analogs typically differ from naturally occurring peptides at one, two or a few positions, often by virtue of conservative substitutions.

Some analogs may also include unnatural amino acids or modifications of N or C terminal amino acids at one, two or a few positions. Examples of unnatural amino acids, without limiting to, are D-amino acids, alpha, alpha-disubstituted amino acids, N-alkyl amino acids, lactic acid, 4-hydroxy-proline, y-carboxyglutamate, epsilon-N,N,N-tri methyllysine, epsilon-N-acetyllysine, O-phosphoserine, N-acetylserine, N-formylmethionine, 3-methylhistidine, 5-hydroxylysine, omega-N-methylarginine, and isoaspartic acid.

The terms "protecting moiety" and "PRO" are interchangeable and refer to any moiety capable of protecting the peptide conjugate of the present invention from adverse effects such as proteolysis, degradation or clearance, or alleviating such adverse effects.

In some embodiments, the protecting moiety may be an alpha-amino protecting moiety. In some embodiments, the protecting moiety may be tosyl (a tosyl group) or derivatives thereof.

In some embodiments, the alpha-amino protecting moiety may be tosyl.

In some embodiments the protecting moiety is selected from the group consisting of t-butyloxycarbonyl (BOC, $(CH_3)_3COCO$—, t-BOC), t-amyloxycarbonyl, adamantyl-oxycarbonyl, and p-methoxybenzyloxycarbonyl, 9-fluorenylmethoxycarbonyl (FMOC), 2-chlorobenzyloxycarbonyl and the like, nitro, tosyl ($CH_3C_6H_4SO_2$—), benzyloxycarbonyl (CBZ), adamantyloxycarbonyl, 2,2,5,7,8-pentamethylchroman-6-sulfonyl, 2,3,6-trimethyl-4-methoxyphenyl-sulfonyl, t-butyl benzyl (BZL) or substituted BZL, such as, p-methoxybenzyl, p-nitrobenzyl, p-chlorobenzyl, o-chlorobenzyl, and 2,6-dichlorobenzyl. Each possibility represents a separate embodiment of the present invention.

In some embodiments, PRO may be selected from t-butyl, cyclohexyl, cyclopentyl, benzyloxymethyl (BOM), tetrahydropyranyl, trityl, chlorobenzyl, 4-bromobenzyl, and 2,6-dichlorobenzyl. Each possibility represents a separate embodiment of the present invention.

Other protecting groups which may suitably employed are bromobenzyloxycarbonyl, xanthyl (Xan) and p-methoxy-benzyl. Each possibility represents a separate embodiment of the present invention.

In some embodiments, PRO may be tosyl.

The terms "protease-disabling moiety" and "DIS" as used herein are interchangeable and refer to any moiety capable of binding to a protease and transiently or permanently disabling its proteolytic activity. In some embodiments, the protease-disabling moiety may be a thrombin-disabling moiety. In some embodiments, the protease disabling moiety may be a thrombin inhibitor.

In some embodiments, the protease-disabling moiety may be a protease-disabling compound selected from irreversible inhibitors and reversible inhibitors.

In some embodiments, the protease-disabling moiety may be an irreversible inhibitor selected from the group consisting of substituted acetyl (1-x-actyl), sulfonylfluorides (—SO$_2$F), chloromethylketones (—COCH$_2$Cl), esters (—COOR), boronic acids (—B(OR)$_2$) and combinations thereof.

In some embodiments, the protease-disabling moiety may be a reversible inhibitor selected from the group consisting of aldehydes (—CHO), arylketones (—CO-Aryl), trifluoromethylketones (—COCF$_3$) ketocarboxylic acids (—COCOOH) and combinations thereof.

In some embodiments the protease-disabling moiety may be a protease-disabling compound selected from the group consisting of chloromethylketone (CK) and derivatives thereof, sulfonylfluorides (—SO$_2$F), chloromethylketones (—COCH$_2$Cl), esters (—COOR), boronic acids (—B(OR)$_2$), aldehydes (—CHO), arylketones (—CO-Aryl), trifluoromethylketones (—COCF$_3$) and ketocarboxylic acids (—COCOOH).

In some embodiments, the protease-disabling moiety may be a substituted acetyl. In some embodiments, the substituted acetyl may be haloacetyl. In some embodiments, the haloacetyl may be chloroacetyl. In some embodiments, the protease-disabling moiety may be chloromethylketone (CK).

In some embodiments, the peptide conjugate may be tosyl-DPR-CK. In some embodiments, the peptide conjugate may be tosyl-LDPR-CK. In some embodiments, the peptide conjugate may be tosyl-TLDPR-CK. In some embodiments, the peptide conjugate may be tosyl-ATLDPR-CK. In some embodiments, the peptide conjugate may be tosyl-NATLDPR-CK.

In some embodiments, the peptide conjugate may be tosyl-PEP-CK, wherein PEP is Aspartic acid-Proline-Arginine or any one of the peptides set forth in SEQ ID NOs: 1-17, or an active variant thereof, wherein CK may be bound to the C'-terminus amino-acid of Arginine and tosyl may be bound to the N'-terminus amino acid of PEP.

Several thrombin inhibitors are known in the art, including T-L-C-K (also known as N alpha-tosyl-L-lysine chloromethyl ketone or TLCK), NAPAP (also known as Na-(2-naphthyl-sulphonyl-glycyl)-DL-p-amidinophenylalanyl-piperidine), PN-1 (also known as Protease nexin-1), PN-2 (also known as Protease nexin-2, APP) and SCH79797 (also known as N3-Cyclopropyl-7-[[4-(1-methylethyl)phenyl]methyl]-7H-pyrrolo[3,2-f]quinazoline-1,3-diamine dihydrochloride). TLCK is an irreversible inhibitor of the serine protease trypsin (inactivates trypsin most rapidly at pH 7.5), and many trypsin-like serine proteases. The histidine-46 residue located in the active site of trypsin is alkylated by TLCK. NAPAP binds thrombin in the S1, S2 and S4 pockets. The amidine group on NAPAP forms a bidentate salt-bridge with Asp deep in the S1 pocket, the piperidine group takes the role of proline residue and binds in the S2 pocket, and the naphthyl rings of the molecule forms a hydrophobic interaction with Trp in the S4 pocket. PN-1 is a 43 kDa thrombin inhibitor, member of the serine protease inhibitor superfamily (serpins), which regulates matrix accumulation and coagulation under pathophysiologic conditions by inhibiting thrombin, plasmin, and tissue plasminogen activators. PN-2 is a protease inhibitor, which is the secreted form of the amyloid beta-protein precursor (APP) which contains a Kunitz protease inhibitor domain. SCH79797 is a potent and selective non-peptide antagonist of protease activated receptor-1 (PAR-1).

However, the alleged therapeutic effect of the known inhibitors is accompanied by serious adverse effects. For example, as detailed below, the very short peptide T-L-C-K, induced inhibition of glioma-cell proliferation, at relatively high concentrations (mM) but caused severe internal bleeding.

Surprisingly, the peptide conjugates of the invention, which are based on the thrombin binding site on PAR-1, provide the required therapeutic effect without causing mortal side effect. As exemplified hereinbelow, the peptide conjugates were shown to effectively inhibit glioma growth and thrombin activity.

In some embodiments, the N' terminal amino acid of PEP may covalently bind to PRO, directly or via a linker, through its N' amino-group or through its side-chain. In some embodiments, the C' terminal amino acid of PEP may covalently bind to DIS, directly or via a linker, through its C' carboxyl-group or through its side-chain.

In some embodiments, PRO may be bound to PEP via a linker.

The term "linker" as used herein refers to any molecule bound to both PRO and PEP and/or to both PEP and DIS. In its simplest form, a linker may be a covalent bond. More elaborate linkers may be amino-acid moieties, peptide moieties, nucleotide moieties, oligonucleotide moieties etc. Contemplated linkers may also serve a further therapeutic purpose, for example, they may be fluorescent, thereby enabling detection of the peptide conjugates carrying them, or they may be a polyethylene glycol (PEG) moiety, further protecting the peptide conjugates carrying them from degradation. Thus, in some embodiments, said linker may be selected from the group consisting of a peptide linker and an oligonucleotide linker. Each possibility represents a separate embodiment of the present invention.

In some embodiments, there is provided a pharmaceutical composition, comprising the peptide conjugate described above, as a pharmaceutically active ingredient, and a pharmaceutically acceptable carrier. In some embodiments, the pharmaceutical composition may further comprises trichloroacetate (TCA) salt.

The term "pharmaceutically acceptable carrier" as used herein refers to any of the standard pharmaceutical carriers known in the field such as sterile solutions, tablets, coated tablets, and capsules. Typically, such carriers contain excipients such as starch, milk, sugar, certain types of clay, gelatin, stearic acids or salts thereof, magnesium or calcium stearate, talc, vegetable fats or oils, gums, glycols, or other known excipients. Such carriers may also include flavor and color additives or other ingredients.

Examples of pharmaceutically acceptable carriers include, but are not limited to, the following: water, saline, buffers, inert, nontoxic solids (e.g., mannitol, talc).

Compositions comprising such carriers are formulated by well-known conventional methods. Depending on the intended mode of administration and the intended use, the compositions may be in the form of solid, semi-solid, or liquid dosage forms, such, for example, as powders, granules, crystals, liquids, suspensions, liposomes, nano-particles, nano-emulsions, pastes, creams, salves, etc., and may be in unit-dosage forms suitable for administration of relatively precise dosages.

In some embodiments, the pharmaceutical composition of the invention may be formulated for oral, nasal, aerosol, inhalational, abdominal, subcutaneous, intra-peritoneal or intravenous administration. Each possibility represents a separate embodiment of the present invention.

In some embodiments, the pharmaceutical composition of the invention may be for intravenous administration.

In some embodiments, there is provided use of a peptide conjugate as described above, for the treatment of a disease or disorder associated with excessive protease activity.

In some embodiments, the use of the peptide conjugate may further include use of a second therapeutic agent. In some embodiments, the second therapeutic agent may be a PAR-1 antagonist.

As used herein, the term 'excessive protease activity' refers to activity which is at least twice as high as normal activity of the protease. In some embodiments, excessive protease activity refers to an activity that is at least three times higher the normal activity of the protease. For example, typical excess activity of protease in stroke, diabetes, ALS, EAE, trauma and glioma is two to three times higher than the protease activity in control subjects. In another example, the excess activity in stroke is up to 100 times higher than the protease activity in control subjects.

The term "disease or disorder associated with excessive protease activity" as used herein refers to any disease or disorder known to be caused and/or manifested by a higher than normal protease activity, as determined by standard methods well known in the art.

In some embodiments, there is provided a method for treating a disease or disorder associated with excessive protease receptor activity comprising administering to a subject in need thereof, a pharmaceutical composition comprising a peptide conjugate according to the present invention and a carrier, In some embodiments, said disease or disorder may be selected from the group consisting of neuroinflammation, neuroinflammatory diseases or disorders, neurodegenerative disease or disorder, neuropathy, and diabetes-related neuropathy. Each possibility represents a separate embodiment of the present invention.

Diabetic peripheral neuropathy (DPN), one of the most prevalent forms of diabetes-related neuropathy, principally manifests itself as sensory loss and weakness of the lower limbs and ultimately accounts for significant morbidity contributing to amputation. In the PNS the prototypical inflammatory disease affecting nerve cells is the Guillain-Barré syndrome (GBS). GBS is a group of acute inflammatory neuropathies and its animal model is experimental autoimmune neuritis (EAN). Acute inflammatory demyelinating polyneuropathy (AIDP) is the most common form of GBS, and is characterized by demyelination of peripheral axons and axonal degeneration in severe cases. The mechanism leading to GBS are still being elucidated and most of the evidence points to an immune attack at the node of Ranivier including the glial components. Amyotrophic lateral sclerosis (ALS) also affects peripheral nerve by causing selective degeneration of lower motor nerves together with degeneration of upper motor neurons in the brain. The cause of this disease is not known and treatment for it is limited to the use of riluzol, a glutamate receptor antagonist, which is only partially effective and patients with this disease will die within 2 years of diagnosis.

In some embodiments, said diseases or disorders may be selected from the group consisting of: glioma, astrocytomas, glioblastoma, oligodendroglioma, ependymoma, mixed gliomas glioblastoma multiforme, neuropathy, diabetic peripheral neuropathy, Guillain-Barré syndrome, amyotrophic lateral sclerosis, acute inflammatory demyelinating polyneuropathy, acute disseminated encephalomyelitis, optic neuritis, transverse myelitis, neuromyelitis optica, Alzheimer's disease, Huntington's disease, amyotrophic lateral sclerosis, epilepsy, multiple sclerosis and Parkinson's disease. Each possibility represents a separate embodiment of the present invention.

In some embodiments, treating may include any one or more of inhibiting the progression of said disease or disorder, attenuating the progression of said disease or disorder or preventing deterioration of said disease or disorder. Each possibility represents a separate embodiment of the present invention.

In some embodiments, there is provided use of a peptide conjugate described above, for the preparation of a medicament for the treatment of a disease or disorder associated with excessive protease receptor activity. Each possibility represents a separate embodiment of the present invention.

In some embodiments, there is provided a method of treating a disease or disorder associated with excessive protease receptor activity in a patient in need of such treatment, comprising administering a therapeutically effective amount of the pharmaceutical composition described above to said patient, thereby treating said disease or disorder. Each possibility represents a separate embodiment of the present invention.

In some embodiments, the method of treating the disease or disorder may further include administering a second therapeutic agent. In some embodiments, the second therapeutic agent may be a PAR-1 antagonist.

There is provided a kit comprising a peptide conjugate for the treatment of a disease or disorder associated with excessive protease receptor activity, wherein the peptide conjugate may be as set forth in formula I:

$$\text{PRO-PEP-DIS} \qquad (I)$$

wherein, PRO is a protecting moiety; PEP is a peptide moiety comprising Aspartic acid-Proline-Arginine, or an active variant thereof; and DIS is a protease-disabling moiety, and wherein PRO is bound to the N'-terminus amino acid of PEP directly or via a linker, and wherein DIS is bound to the C'-terminus amino acid of PEP directly or via a linker.

In some embodiments, the kit may further include instructions for use of the pharmaceutical composition for the treatment of the disease or disorder. In some embodiments, the instructions may further recite a web site address providing further information, and troubleshooting among other services. In some embodiments, the instructions may be on paper form such as a package insert or label.

In some embodiments, the methods of the invention are aimed at preventing excessive protease receptor activity, including, preventing the onset of excessive protease receptor activity. Determining the dose of the peptide conjugate required for preventing protease receptor activity may be carried out by assessing reduction in the PAR-1 levels following administration of the peptide conjugate of the invention. Reduction in excessive protease receptor activity refers to a decrease in, or an absence of, activity of the receptor relative to the levels of activity prior to administration or relative to a control value. Reduced PAR-1 activity, includes reduction of activity by at least about 10% (e.g., 20%, 30%, 40%, 50%, 60%, 70%, 80%, or 90%), as compared to the level of activity just prior to administration. Hence, the level of activity obtained from a sample of a patient in need thereof may be compared to the level of PAR-1 activity in a sample obtained from said patient in previous time points (e.g., prior to administration of the peptide conjugate or during the onset of a neuropathic disease or disorder). It is further optional to measure PAR-1 activity in an individual prior to the onset of a disease or disorder (e.g., during a regular check-up), in order to determine the individual's baseline.

The PAR-1 activity in a patient in need thereof may be compared to a standard or control obtained from normal individuals. In one example, PAR-1 activity can be assessed in a population of healthy individuals or individuals who have not had a neuropathic disease or disorder. Such activity is referred to as a "negative control." Conversely, PAR-1 may also be obtained from a pool of individuals who are undergoing a neuroinflammation, neuroinflammatory diseases or disorders, neurodegenerative disease or disorder, neuropathy, or diabetes-related neuropathy, in order to obtain a "positive control." Thus, in some embodiments, following administration of the peptide conjugate of the invention, the activity level of PAR-1 may decrease; the level(s) may get closer to the level of the negative control, and farther from the positive control. Alternatively, the PAR-1 levels of activity decrease as compared to the levels during the onset of the aforementioned disease or disorder.

The terms "comprises", "comprising", "includes", "including", "having" and their conjugates mean "including but not limited to". This term encompasses the terms "consisting of" and "consisting essentially of". As used herein, the singular form "a", "an", "the" and "said" include plural references unless the context clearly dictates otherwise. For example, the term "a compound" or "at least one compound" may include a plurality of compounds, including mixtures thereof.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Example 1. Thrombin-Like Activity in Sciatic Nerves of Diabetic Rats

Figure 1B:
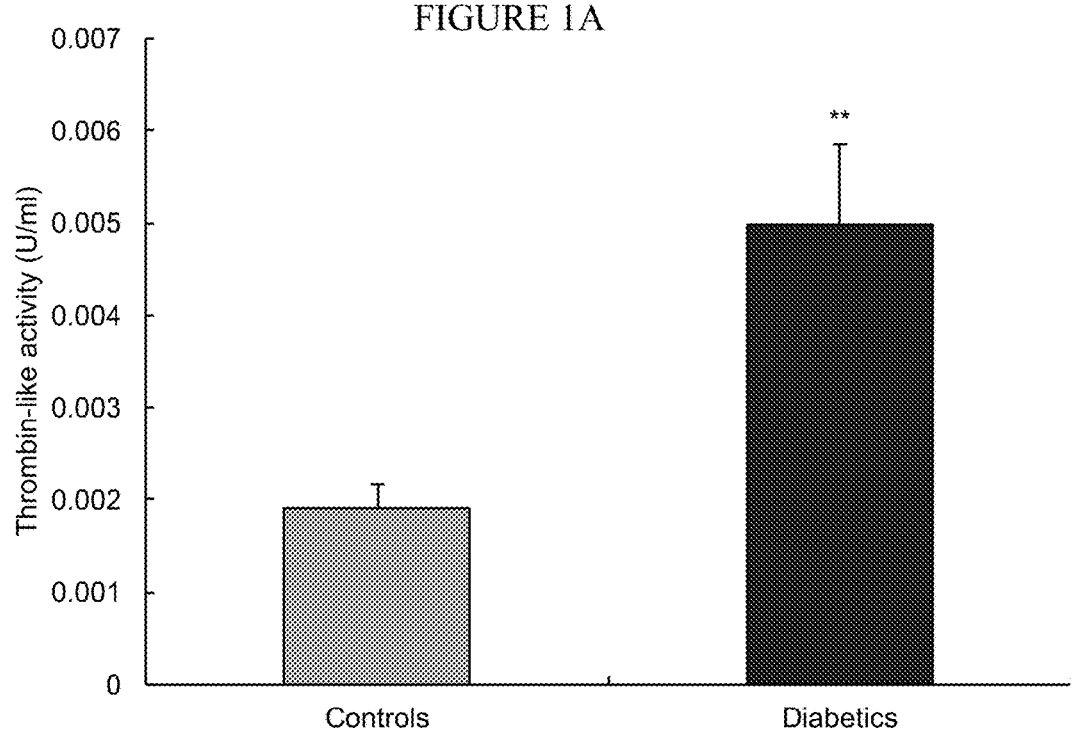

Thrombin-like activity was measured in sciatic nerves derived from animal models of Guillain-Barré Syndrome (termed EAN, for experimental autoimmune neuritis; FIG. 1A) and diabetes (streptozotocine (STZ)-induced diabetes; FIG. 1B).

As presented in FIG. 1 the soluble thrombin-like activity generated by, and released from, sciatic nerves of EAN or diabetic (STZ) rats, into the surrounding medium, was compared to thrombin-like activity in healthy control rats (n=12) and in CFA rats (complete Freund's adjuvant). The latter control group refers to rats treated with an inoculums containing the mycobacterium tuberculosis emulsified in saline and CFA only. The results indicate that thrombin-like activities were significantly elevated in EAN rates 10 days after induction (Data is presented as a mean thrombin like activity U/ml±SEM, **=p<0.01; *=p<0.005).

The results further indicate that thrombin-like activities were significantly elevated in diabetic rats (FIG. 1B, **=p=0.00071).

Figure 20A:
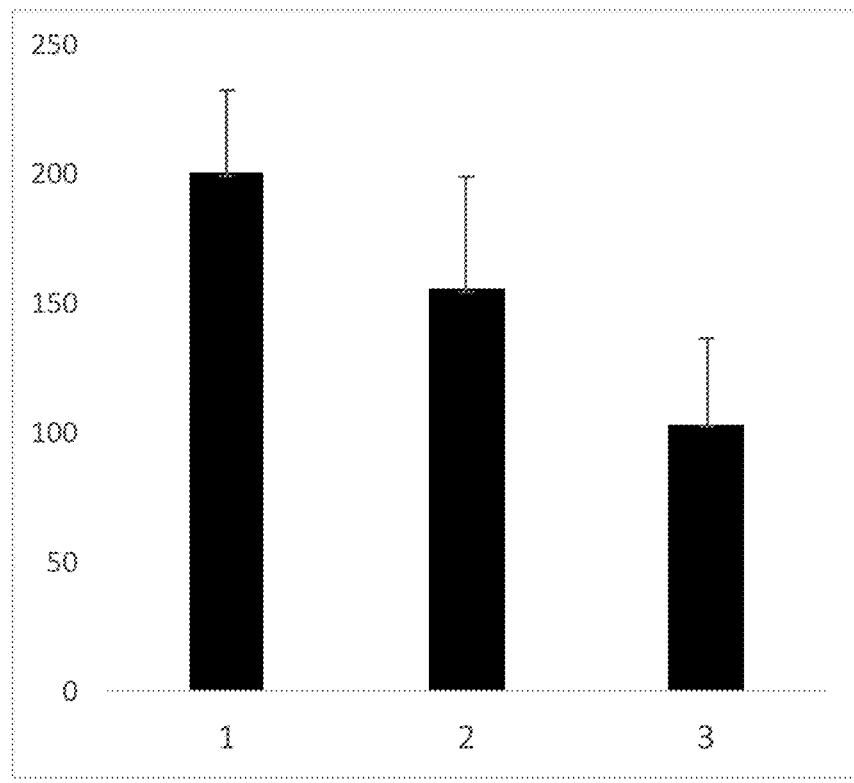
FIG. 20 presents changes in tumor size (A) and in the size of edema surrounding the tumor (B) in 3 groups of rats: (1) control; (2) treatment with 2 µM of a peptide conjugate comprising the peptide termed 6AA (SEQ ID NO: 3); and (3) treatment with 20 µM of a peptide conjugate comprising the peptide termed 6AA (SEQ ID NO: 3).
Figure 20B:
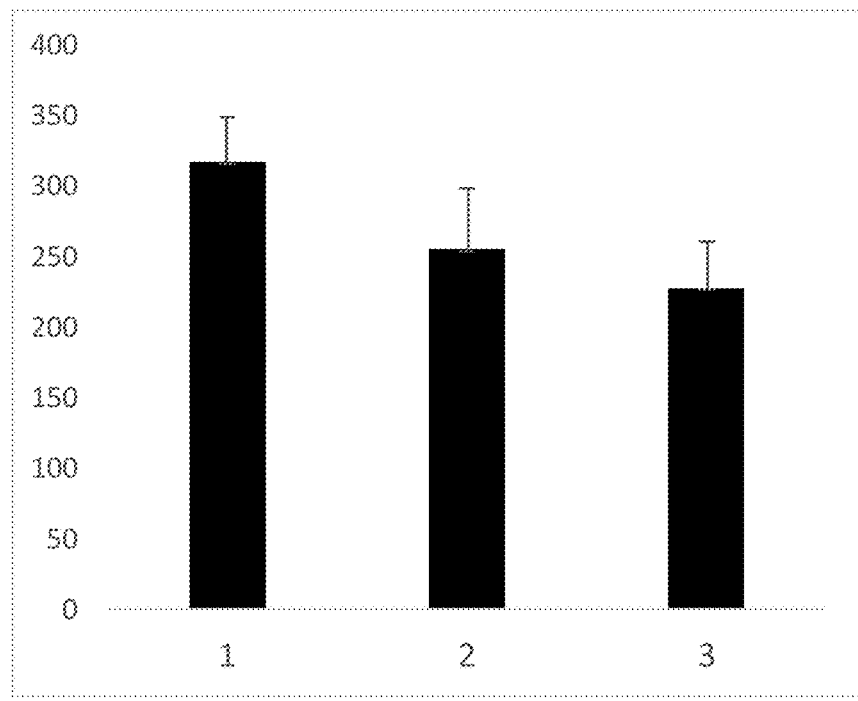

The conduction velocity of sciatic nerves derived from an animal model of diabetes (streptozotocine (STZ)-induced diabetes; FIG. 20) was measured in mice treated daily with sham (STZ), or with the active drug TLDPR (peptide 5AA; SEQ ID NO: 2) nested between N alpha-tosyl and chloromethyl ketone, namely TTN-ATLDPR-CK (termed hereinafter T5AACK) injected in 100 microliter of 10 nM, 100 nM and 1 micromolar.

Conduction velocities in the sciatic nerves of the mice were assessed by standard electrophysiology nerve conduction methods by a blind assessor. The nerve conduction studies were carried out one month after the induction of diabetes. A group of normal mice without diabetes served as controls. All STZ treated mice developed severe diabetes.

The comparison of sham treated and T5AACK 1 micromolar treated mice was highly significant, resulting with p=0.00046 (T-test) and the effect of the 10 nM dose followed a similar trend, resulting with p=0.016 (FIG. 20).

Thus, elevated thrombin-like activity in diabetic rats and mice represents a potential target for intervention by the new conjugates of the present invention.

Example 2. PAR-1 Expression Level in Sciatic Nerves of Diabetic Rats

Figure 2A:
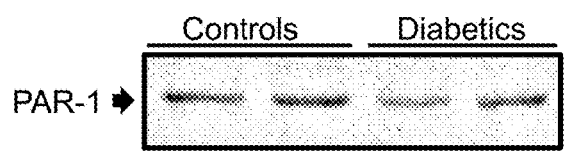
FIG. 2 shows Western blots (A, C) and the corresponding statistical analyses (B, D) from 3 independent experiments of PAR-1 immunoreactivity (A, B) and PN-1 immunoreactivity (C, D) in desheathed sciatic nerve from STZ-induced diabetic rats (n=3) and control non-diabetic rats (n=3; *=p<0.05; **=p<0.01).
Figure 2B:
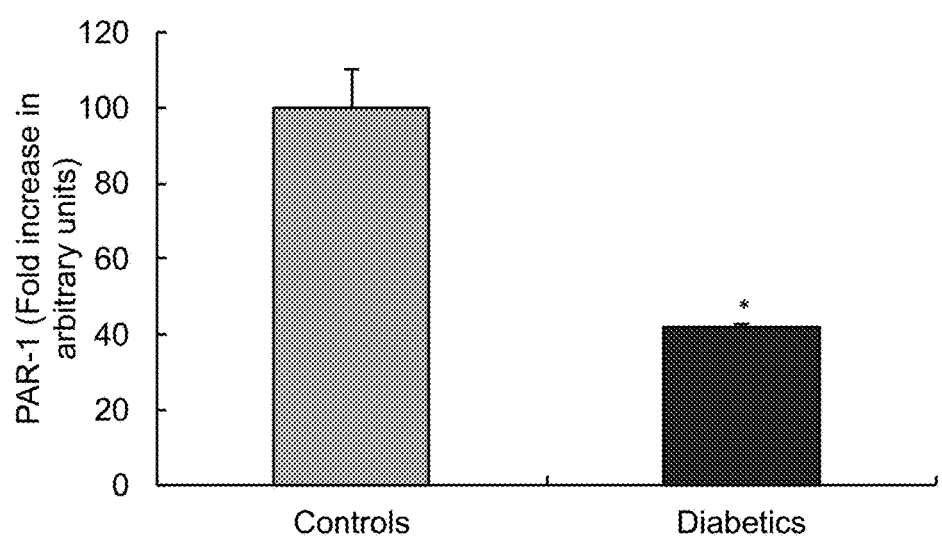
Figure 2C:
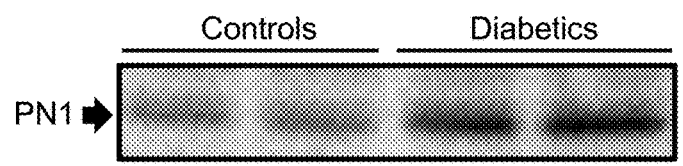
Figure 2D:
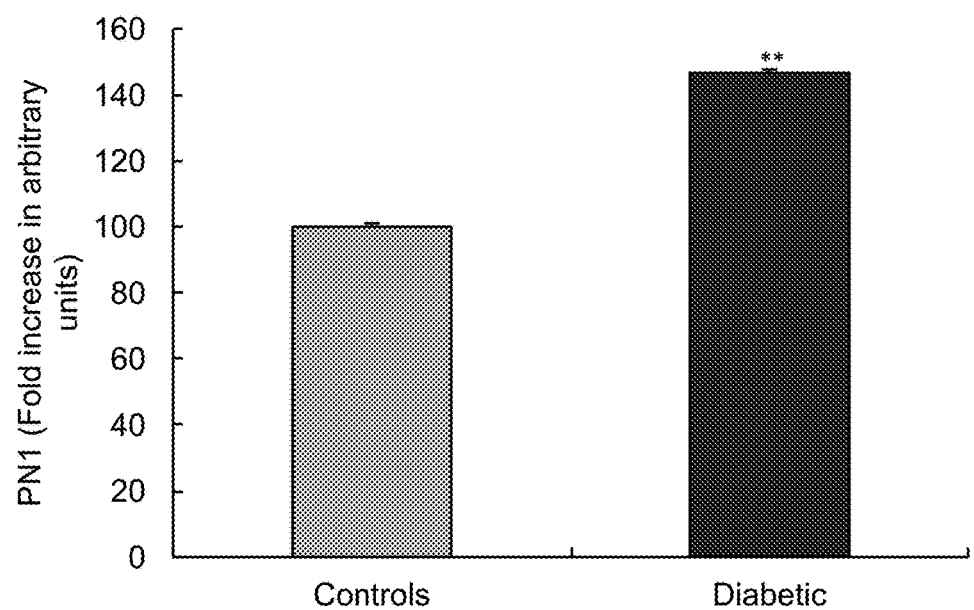

The expression level of PAR-1 was measured in desheathed sciatic nerves from STZ-induced diabetic rats and control non-diabetic rats (FIG. 2A-2B).

Western blot analysis of PAR-1 level from sciatic nerves of two STZ-induced rats, as compared to two healthy controls indicates a significant decrease in PAR-1 level in STZ-induced rats sciatic-nerves (n=3; p=0.012) compared to control non-diabetic rats (FIG. 2B; data presented as a mean fold±SEM, *=p<0.05).

Based on FIG. 2 and further data (not disclosed) significantly low levels of PAR-1 are found in the animal models of Guillain-Barré Syndrome (EAN) and diabetes (STZ-induced diabetic rats). Without being bound by any theory or mechanism, such findings may indicate an intrinsic protection mechanism employed by the nerves to avoid PAR-1 over activation by the elevated thrombin-like activities (such as presented in FIG. 1B). Thus, PAR-1 sensitivity may strengthen the need to interfere with the PAR-1 pathway and protect the receptor from over-activation.

Example 3. PN-1 Expression Level in Sciatic Nerves of Diabetic Rats

Figure 3A:
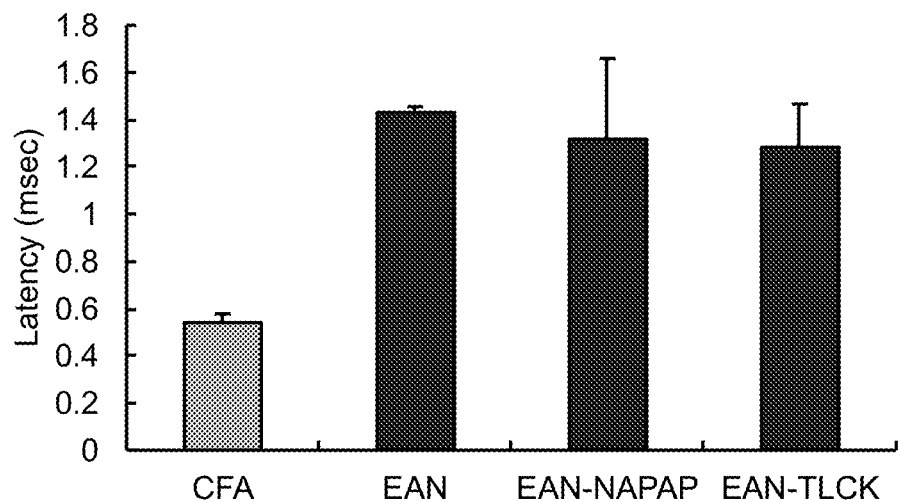
FIG. 3 presents the effect of (i) N alpha-tosyl-L-lysine chloromethyl ketone (TLCK, 4.4 mg/kg, n=5) and (ii) Na-(2-naphthyl-sulphonyl-glycyl)-DL-p-amidinophenylalanyl-piperidine (NAPAP, NAPAP-120 µM/kg body weight, n=5), treatments (black bars) relative to control/CFA (grey bars, n=3) and relative to EAN untreated rats (EAN, n=5) through electrophysiological tests: latency (A), conduction velocity (B) and amplitude (C). Statistics are indicated as follows: *=p<0.05, **=p<0.01.
Figure 3B:
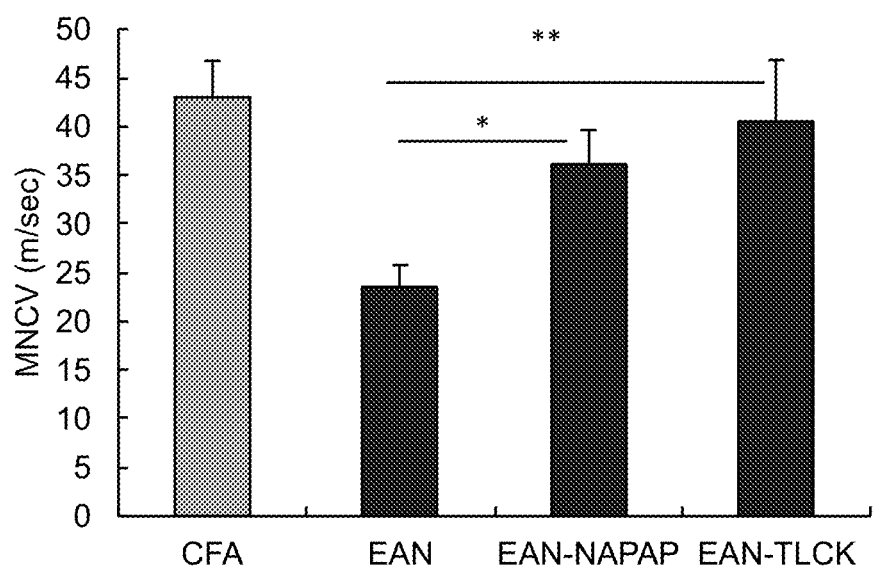

The expression level of PN-1 (thrombin-inhibitor, 143 kDa) was measured in desheathed sciatic nerves from STZ-induced diabetic rats and control non-diabetic rats, by Western blot analysis (FIGS. 3A-3B).

The result show a significant increase in PN-1 level in STZ-induced rats sciatic-nerves (p=0.003) compared to control non-diabetic rats (FIG. 3B; data presented as a mean fold±SEM, **=p<0.01).

Without being bound by any theory or mechanism, increased levels of thrombin inhibitors, such as PN-1, in STZ-induced diabetic rats is potentially an intrinsic protection mechanism employed by the nerves to avoid PAR-1 over activation by the elevated thrombin-like activities presented in FIG. 1. In addition, the increased thrombin-inhibitor levels in diabetic rats may indicate the need to regulate PAR-1 activating-proteases.

Figure 3C:
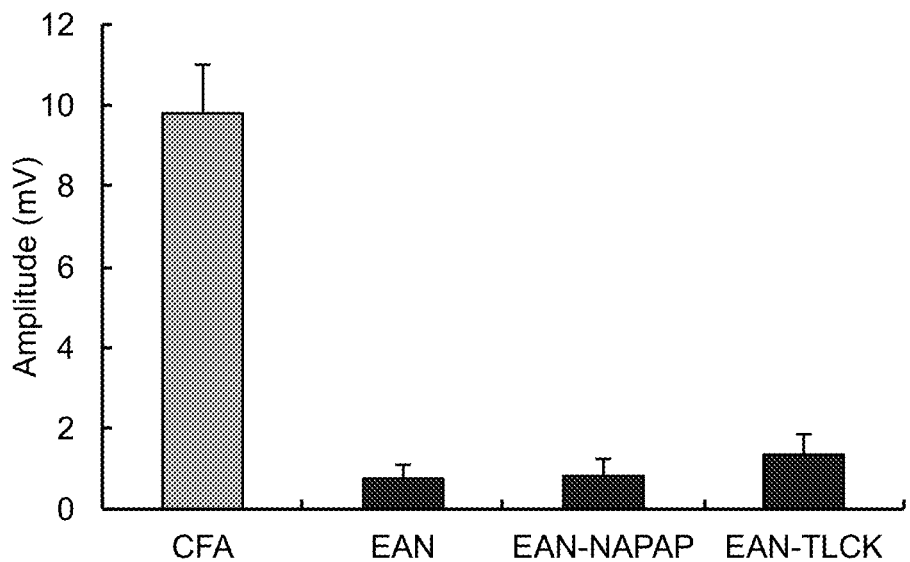
Figure 4A:
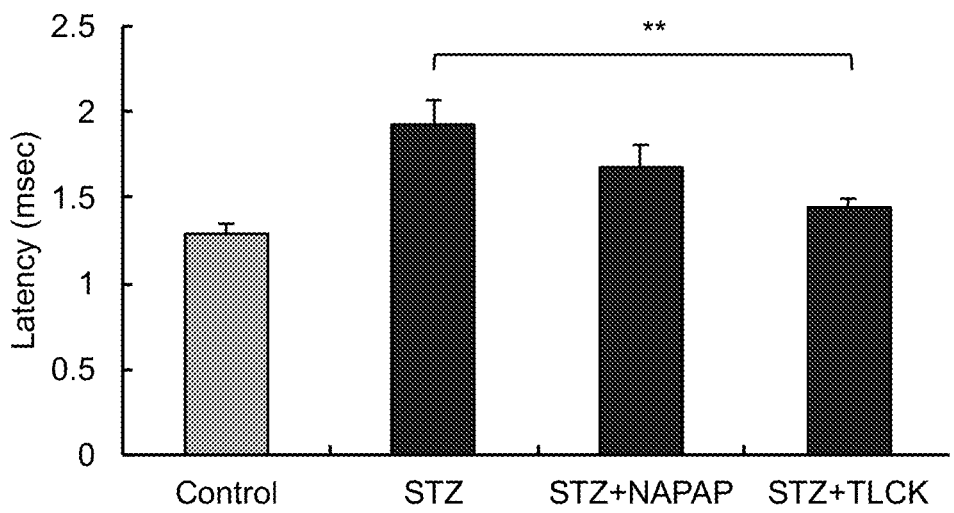
FIG. 4 shows the effect of N alpha-tosyl-L-lysine chloromethyl ketone (TLCK, 4.4 mg/kg body weight, n=8) and (ii) Na-(2-naphthyl-sulphonyl-glycyl)-DL-p-amidinophenylalanyl-piperidine (NAPAP, 120 µM/kg body weight, n=5), treatments (black bars) relative to control (grey bars, n=4) and STZ-induced diabetic untreated rats (n=5) through electrophysiological tests: latency (A), conduction velocity (B) and amplitude (C). *=p<0.05, **=p<0.01.
Figure 4B:
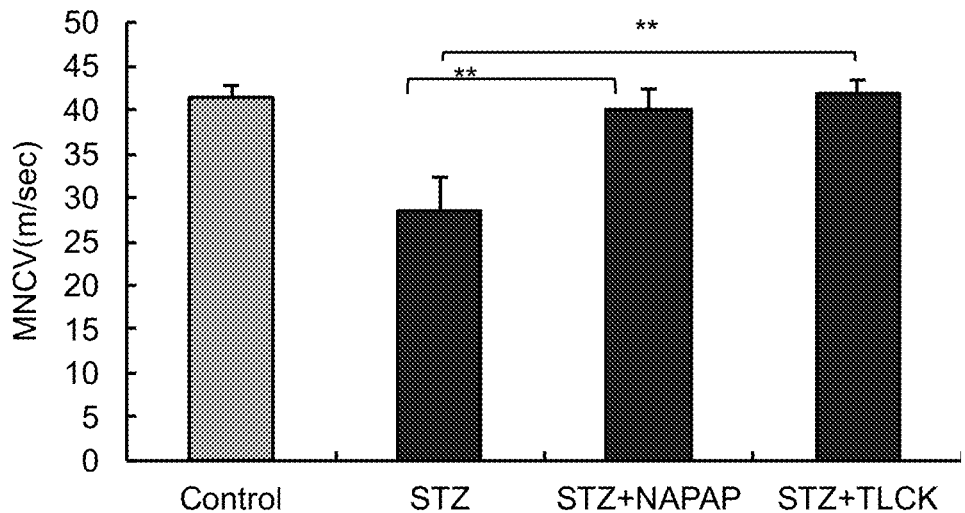
Figure 4C:
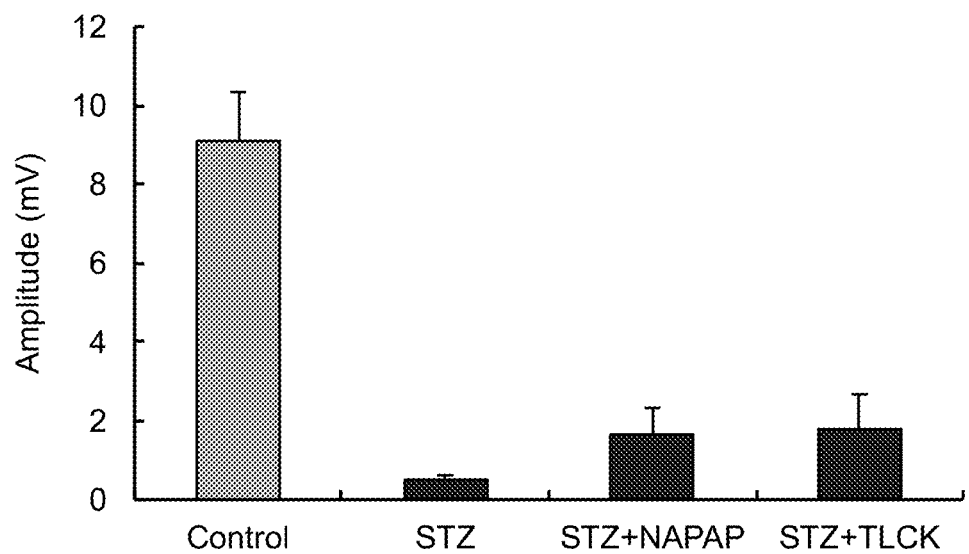

Example 4. Therapeutic Effect of Thrombin-Inhibitors on Electrophysiological Parameter In Vivo Electrophysiological tests of the sciatic nerves were performed on day 32 PI (post-immunization/induction) in EAN model (FIGS. 3A-C) and 8 weeks after STZ induction (FIG. 4A-C). Rats were anesthetized with Phenobarbital (IP, 24 mg/kg). Two pairs of monopolar needle electrodes were used to stimulate the tail nerves. Stimulating cathodes were inserted to a depth of 4-5 mm at the base of the tail and 4 cm distally. An anode at each location was inserted into the skin (4-5 mm depth) 1 cm proximal to the cathode. A ground electrode was placed between the distal stimulating electrode and the active recording electrode. Electromyography (EMG) recordings of responses of the tail muscles to proximal and distal stimuli, made by a pair of ring electrodes coated with electrode jelly and placed 1 cm distally to the distal stimulating electrode, were collected. The tail skin was wiped with alcohol prior to placing the electrodes. The EMG output was displayed on a fully digital recording Keypoint apparatus (Dantec, Skovlunde, Denmark). Both proximal and distal latencies were measured using time intervals from the stimulus artifact to the first deflection from baseline. To calculate the motor nerve conduction velocity (MNCV), the distance between stimulating cathodes was divided by the latency difference. Amplitudes of the compound muscle action potential (CMAP) from both proximal and distal stimulations were measured from the negative to the positive peaks. The reduction of the proximal CMAP compared with that of the distal CMAP was calculated by the equation: [(distal CMAP-proximal CMAP)/distalCMAP×100] and was defined as the R ratio. Temperature differences were minimized by conducting the study as soon as the anesthesia had taken effect and by warming the tail with a heating lamp.

Data was collected from EAN rats (FIG. 3) and STZ rats (FIG. 4) treated daily with the following thrombin-inhibitors: (i) N alpha-tosyl-L-lysine chloromethyl ketone (TLCK) and (ii) Nα-(2-naphthyl-sulphonyl-glycyl)-DL-p-amidinophenylalanyl-piperidine (NAPAP), for 2 weeks.

FIGS. 3 and 4 each include 3 graphs summarizing the results from electrophysiological tests of treated rats, as follows: distal latency (3A, 4A) referring to the time, in milliseconds, between distal stimulation to recording; conduction velocity (3B, 4B) referring to the distance over time, in meters/seconds; and amplitude (3C, 4C) referring to the size of the response as measured in millivolts.

EAN and STZ rats which were not treated with TLCK or NAPAP (FIG. 3B, 'EAN' bar, and FIG. 4B, 'STZ' bar) exhibited a significantly reduced conduction velocity relative to control (FIGS. 3B and 4B, black bars; *=p<0.05, =p<0.01, *=p<0.001). Conduction velocity in rats treated with TLCK was significantly high compared to the saline treated EAN and STZ control groups (*=p<0.05, =p<0.01, *=p<0.001; STZ+TLCK: 41.95±3.9 m/sec n=8 and STZ: 28.5±2.8 m/sec n=4, p=0.001 FIG. 3B, EAN+TLCK: 40.55±6.7 m/sec n=6 EAN: 23.6±1.2 m/sec n=5, p=0.05). NAPAP treatment group showed some improvement in conduction velocities compared to the unaffected control group (EAN+NAPAP: 36.05±3.57 m/sec, n=5 and EAN: 23.6±1.2 m/sec, n=5, p=0.003, FIG. 3B; STZ+NAPAP: 40.1±2.7 m/sec n=5 and STZ: 28.5±2.8 m/sec n=5, p=0.01, FIG. 4B). TLCK treatment increased proximal amplitude (EAN 0.76±0.33, EAN+NAPAP 0.83±0.4, EAN+TLCK 1.36±0.49), in a non-significant manner (FIG. 3B). The beneficial effect on the proximal amplitude observed in the STZ model (FIG. 4C) was also insignificant: STZ+TLCK 1.81±0.8 (n=8), STZ+NAPAP 1.68±0.64 (n=5) compared to STZ: 0.48±0.13 (n=5).

Latency, the time between induction and nerve conduction, was also measured. The results indicate that in the STZ group an increased latency was 1.93±0.139 msec (n=5) compared to control (1.29±0.057 msec, n=4). The NAPAP and TLCK treatments caused decreased latencies of 1.676±0.132 msec (n=5, p=0.11) and 1.44±0.04 msec (n=5, p=0.0019), respectively. In the EAN group an increased latency was detected (1.43±0.023 msec, n=5) compared to control (0.54±0.03 msec, n=3). The NAPAP and TLCK treatments did not caused decreased latencies (1.32±0.33 msec, n=5, p=0.39, 1.28±0.18 msec, n=5, p=0.27, respectively).

The results indicate that treatment with thrombin inhibitors improves nerve conduction in an animal model for diabetes. This outcome was however accompanied by internal bleeding.

Example 5. PAR-1 Expression Level Ex-Vivo in Brain Homogenates of an Animal Model for ALS (SOD-1 Mice)

The expression level of PAR-1 was measured in brain homogenates derived from SOD-1 and wild type control mice.

Figure 5A:
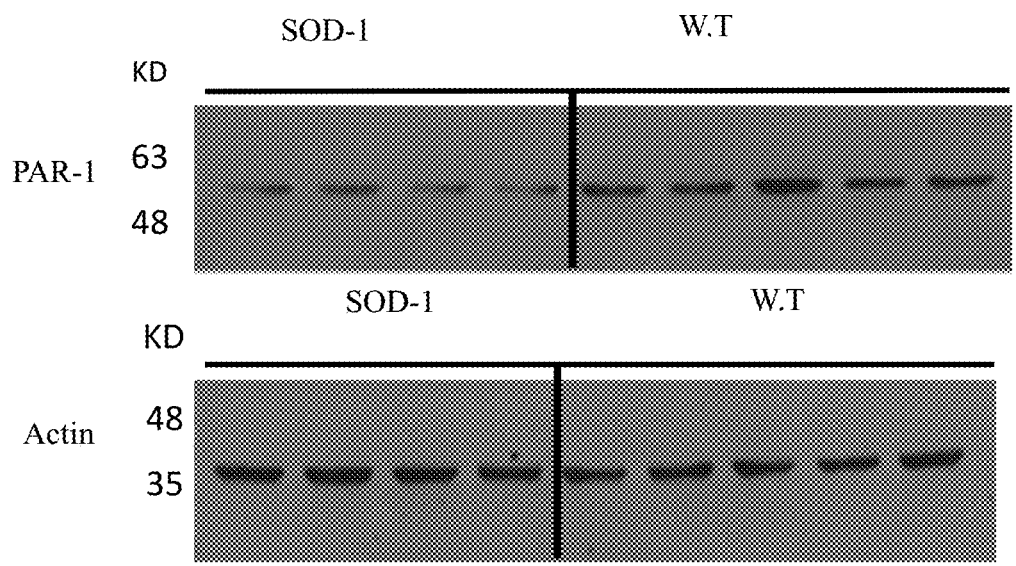
FIG. 5 exhibits Western blots of PAR-1 and actin (A) and a corresponding statistical analysis (B) in brain homogenates derived from SOD-1 and wild-type control mice (p<0.001).
Figure 5B:
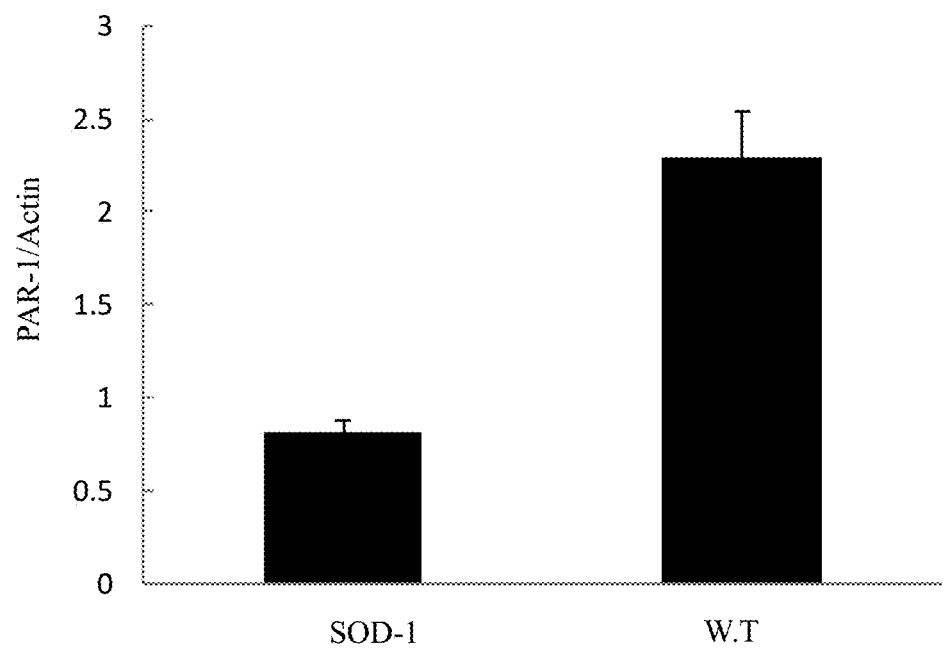

FIG. 5 depicts a Western blots (A) and the corresponding analysis, performed with ImageJ software, from several independent experiments (B), of PAR-1 expression levels in brain homogenates of four SOD-1 mice, as compared to five healthy controls. The results demonstrate a significant decrease (2.8 fold decrease) in the expression of PAR-1 in SOD-1 mice compared to wild-type controls (p<0.001). The results may indicate that interfering with the PAR-1 pathway and protecting PAR-1 from over-activation would be beneficial in treating neuropathic diseases and disorders.

Example 6. Survival Experiment of ALS (SOD-1) Mice Treated with General Thrombin Inhibitors ALS (SOD-1) mice were randomly divided into three groups, and were either untreated (diamond), treated with a relatively general thrombin inhibitor, N alpha-tosyl-L-lysine chloromethyl ketone (4.4 mg/kg TLCK; circle-), or treated with a PAR-1 antagonist (25 µg/kg SCH79797; triangles).

Figure 6:
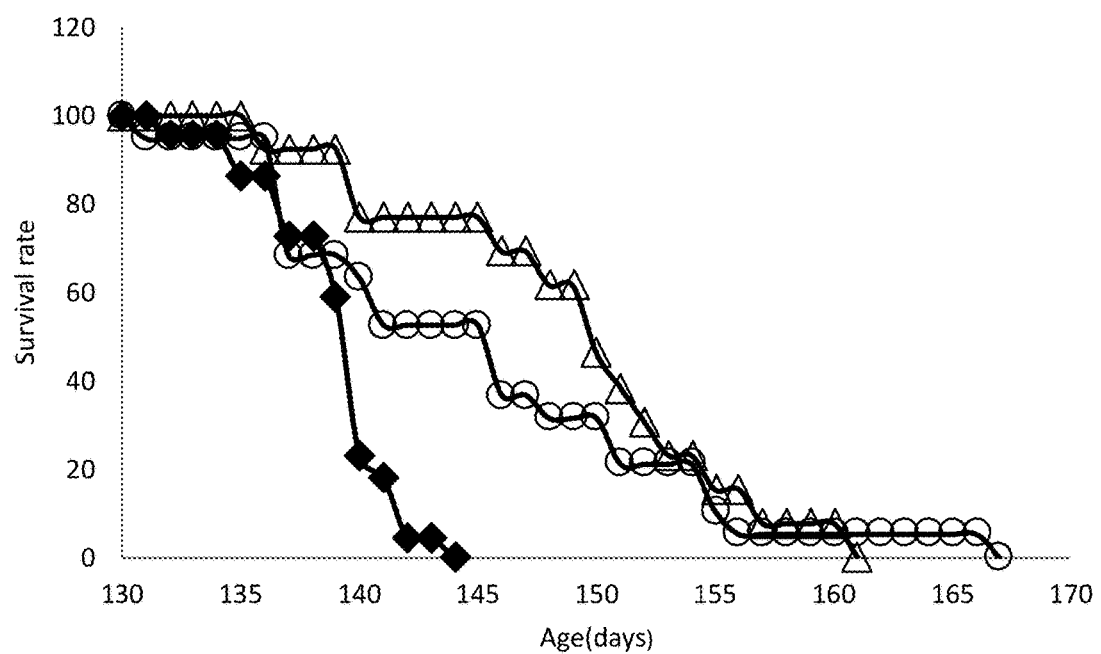
FIG. 6 exhibits a Kaplan-Meier survival curve of (full diamond) untreated (control) SOD-1 mice, (empty circle) SOD-1 mice treated with TLCK (4.4 mg/kg), and (empty triangle) mice treated with PAR-1 antagonist (SCH79797; 25 µg/kg).

The results indicate that survival without treatment did not last more than 145 days. However, treatment with either PAR-1 antagonist or with a thrombin inhibitor improved survival by at least 15 days (FIG. 6). Since PAR-1 is decreased as the disease progresses, utilizing a specific PAR-1-based thrombin inhibitor in advanced stages of the disease seems more reasonable than utilizing a PAR-1 antagonist.

Example 7. Thrombin-Like Activity in Glioma Cell Lines

Figure 7A:
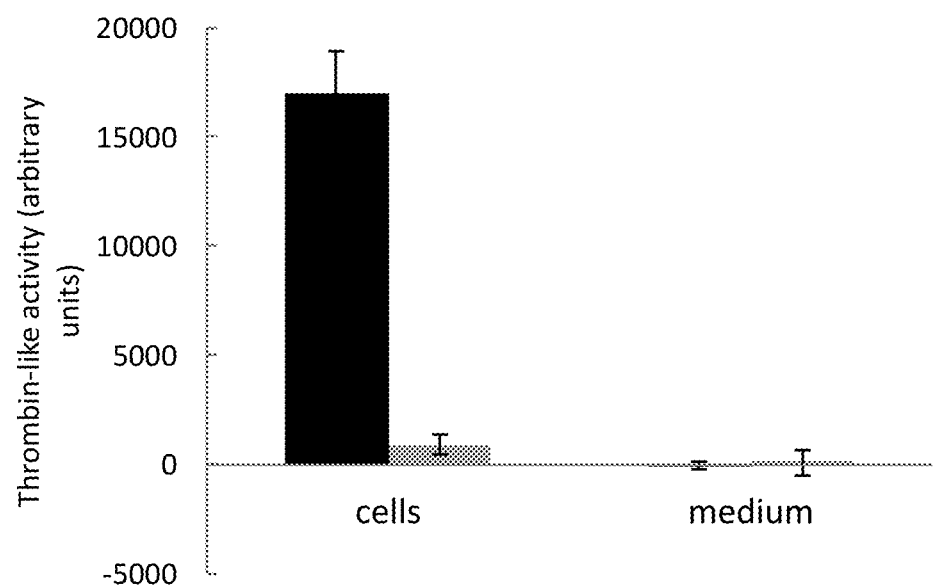
FIG. 7 exhibits the Thrombin-like activity before (black bars) and after treatment with NAPAP (grey bars) in C6 (A) and CNS-1 (B) glioma cells and their surrounding medium.
Figure 7B:
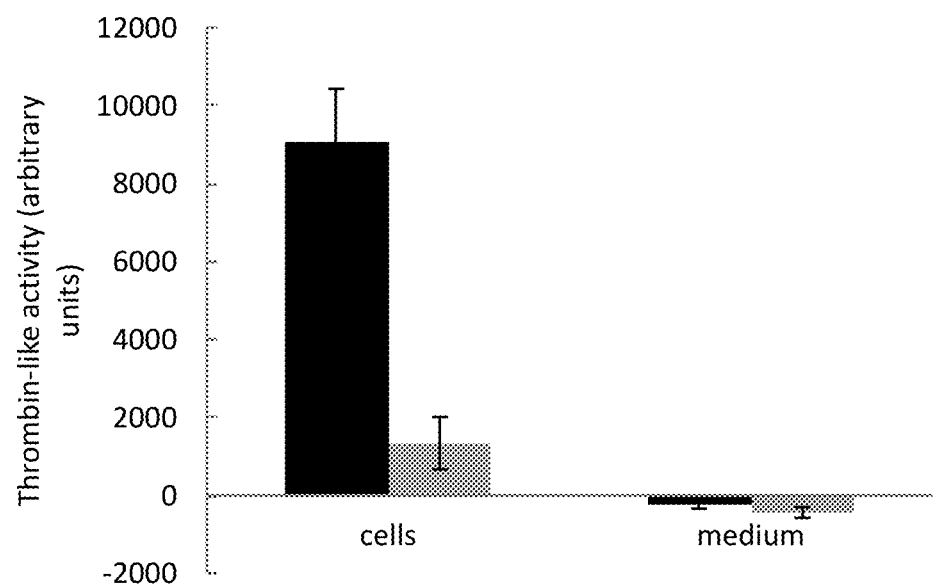

Thrombin-like activity was measured in C6 and CNS-1 glioma cell-lines and their surrounding medium (FIGS. 7A and 7B, respectively), four hours after cells were treated with the highly selective thrombin inhibitor Nα-(2-naphthyl-sulphonyl-glycyl)-DL-p-amidinophenylalanyl-piperidine, NAPAP (FIGS. 7A-7B, grey bars). Results are demonstrated relative to control, non-treated, cells (FIGS. 7A-7B, black bars).

It is evident from FIG. 7 that (a) thrombin-like activity was restricted to the cells themselves, with no apparent activity in the surrounding medium, and (b) thrombin-like activity was inhibited by NAPAP in both cell lines. Since thrombin is known to increase the proliferation of glioma cells, the glioma cell-lines endogenous generation of thrombin-like activity indicates the potential beneficial effect of thrombin specific inhibitor as proliferation regulators in gliomas such as Glioblastoma multiform (GBM).

Example 8. Proliferation-Inhibition of Glioma Cell Lines by a PAR-1 Antagonist

Several peptide moieties (Table 1) according to the present invention were synthesized. Proliferation was measured, by means of XTT, in C6 and CNS-1 glioma cell-lines (FIGS.

Figure 8A:
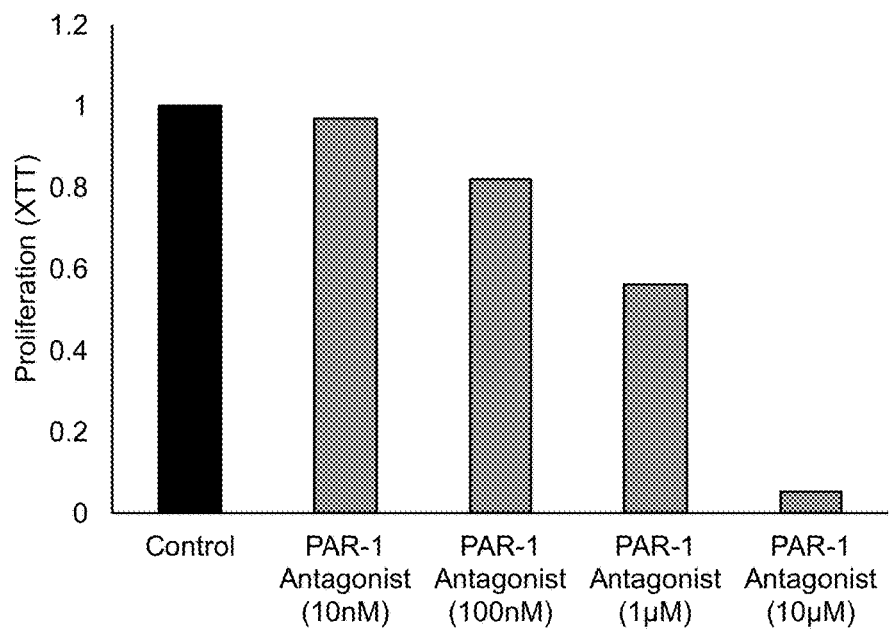
FIG. 8A exhibits proliferation of C6 control cells (black bar) and cells treated with various doses of PAR-1 antagonist SCH79797 (grey bars).
Figure 8B:
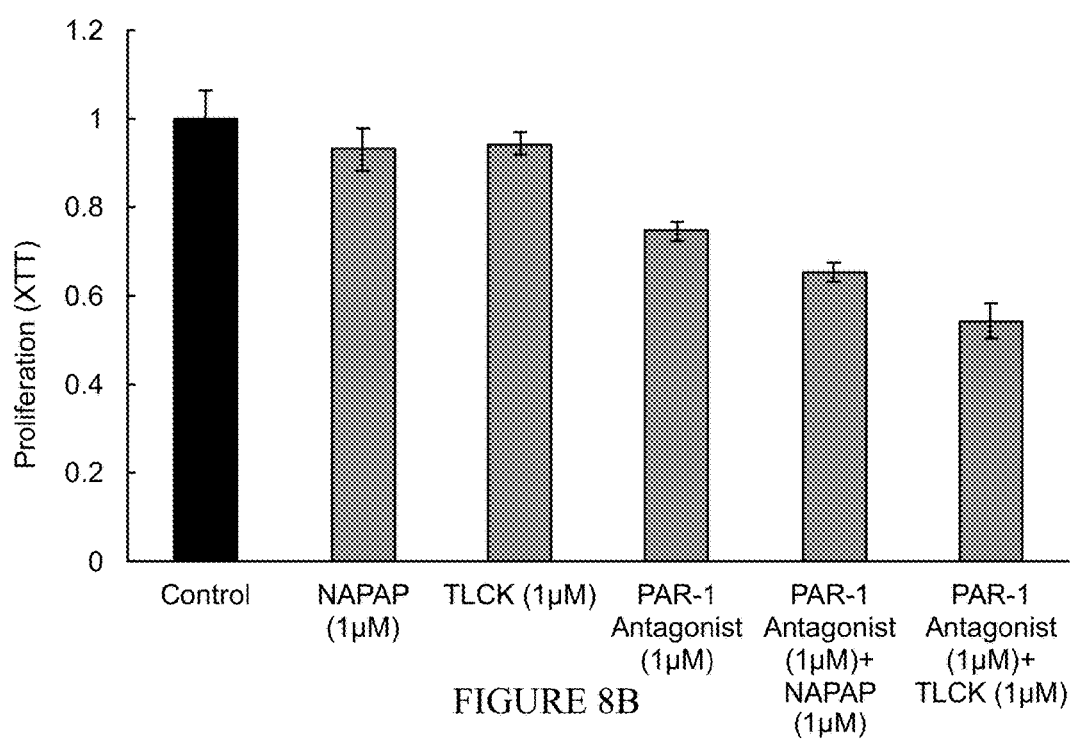
FIG. 8B shows proliferation of CNS-1 control cells (black bar) and cells treated with each of PAR-1 antagonists: SCH79797, NAPAP and TLCK, and combinations thereof (grey bars).

8A and 8B, respectively). In C6 cells, proliferation was measured before (black bar) and after cells were treated with the PAR-1 antagonist SCH79797 at various doses ranging from 10 nM to 10 μM (grey bars; FIG. 8A). In CNS-1 cells, proliferation was measured before (black bar) and after cells were treated with the PAR-1 antagonist SCH79797 (1 μM), the thrombin inhibitor NAPAP, the thrombin inhibitor TLCK, or combinations thereof (grey bars; FIG. 8B).

It is evident from FIG. 8A that the PAR-1 antagonist inhibited proliferation in a dose-dependent manner in C6 cells. Furthermore, according to the results presented in FIG. 8B, NAPAP (1 μM) or TLCK (1 μM) did not inhibit proliferation of CNS-1 cells when administered alone. However, combining NAPAP or TLCK with a PAR-1 antagonist seems to improve the inhibitory effect of the PAR-1 antagonist.

TABLE 1

Amino-acid sequences of peptide moieties.

| SEQ ID | Amino-acid sequence | Peptide Name |
| --- | --- | --- |
| — | DPR | 3AA |
| SEQ ID NO: 1 | LDPR | 4AA |
| SEQ ID NO: 2 | TLDPR | 5AA |
| SEQ ID NO: 3 | ATLDPR | 6AA |
| SEQ ID NO: 4 | NATLDPR | 7AA |
| SEQ ID NO: 5 | TNATLDPR | 8AA |
| SEQ ID NO: 6 | ATNATLDPR | 9AA |
| SEQ ID NO: 7 | KATNATLDPR | 10AA |
| SEQ ID NO: 8 | SKATNATLDPR | 11AA |
| SEQ ID NO: 9 | ESKATNATLDPR | 12AA |
| SEQ ID NO: 10 | PESKATNATLDPR | Segment of the binding site on the receptor PAR-1 |
| SEQ ID NO: 11 | RPESKATNATLDPR | 14AA |
| SEQ ID NO: 12 | RRPESKATNATLDPR | 15AA |
| SEQ ID NO: 13 | ARRPESKATNATLDPR | 16AA |
| SEQ ID NO: 14 | RARRPESKATNATLDPR | 17AA |
| SEQ ID NO: 15 | TRARRPESKATNATLDPR | 18AA |
| SEQ ID NO: 16 | RTRARRPESKATNATLDPR | 19AA |
| SEQ ID NO: 17 | ARTRARRPESKATNATLDPR | C' terminus segment of PAR-1 |
| SEQ ID NO: 18 | LDPRSFLLRNPNDKYEPF | amino-terminal exodomain of PAR-1 |
| SEQ ID NO: 19 | KYEPF | hirudin-like motif |

The peptide moieties were derived from the C'-terminus of PAR-1. A comparison between the amino acid (AA) sequence upstream and downstream to thrombin cleavage-site in human, mouse, rat and bovine indicates that these sequences are by and large conserved (Table 2). The position of the amino acids corresponding to the thrombin cleavage site is indicated for each sequence in the second column of Table 2 and the designed peptide length is indicated in the third column of this Table. Positions 35-47 represent part of the N-terminal of PAR-1, also termed P1-P7, designating the position upstream to the cleavage site.

vide the required activity at significantly lower concentrations and are devoid of harmful side effects, as demonstrated in the following Examples.

Example 9. Inhibition of Cell Proliferation

Initially, CNS-1 glioma cells were treated with increased concentrations of two peptide conjugates: a short conjugate of the formula tosyl-DPR-CK (comprising 3 amino acids, 3AA) or a long conjugate of the formula tosyl-NATLDPR-CK (comprising 7 amino acids, 7AA; SEQ ID NO: 4) in

TABLE 2

PAR-1 amino-acids sequence upstream and downstream to thrombin cleavage-site in human, mouse, rat and bovine.

| Species | Thrombin cleavage site | Position | P7 35 | P6 36 | P5 37 | P4 38 | P3 39 | P2 40 | P1 41 | 42 | 43 | 44 | 45 | 46 | 47 |
|---|---|---|---|---|---|---|---|---|---|---|---|---|---|---|---|
| Human | 41-42 | PEPTIDE | N | A | T | L | D | P | R | S | F | | | | |
| | | 3AA | | | | | D | P | R | | | | | | |
| | | 4AA | | | | L | D | P | R | | | | | | |
| | | 5AA | | | T | L | D | P | R | | | | | | |
| | | 6AA | | A | T | L | D | P | R | | | | | | |
| | | 7AA | N | A | T | L | D | P | R | | | | | | |
| Mouse | 41-42 | PEPTIDE | D | A | T | V | N | P | R | S | F | | | | |
| | | 3AA | | | | | N | P | R | | | | | | |
| | | 4AA | | | | V | N | P | R | | | | | | |
| | | 5SAA | | | T | V | N | P | R | | | | | | |
| | | 6AA | | A | T | V | N | P | R | | | | | | |
| | | 7AA | D | A | T | V | N | P | R | | | | | | |
| Rat | 45-46 | PEPTIDE | Y | A | T | P | N | P | R | S | F | | | | |
| | | 3AA | | | | | N | P | R | | | | | | |
| | | 4AA | | | | P | N | P | R | | | | | | |
| | | 5AA | | | T | P | N | P | R | | | | | | |
| | | 6AA | | A | T | P | N | P | R | | | | | | |
| | | 7AA | Y | A | T | P | N | P | R | | | | | | |
| Bovine | 41-42 | PEPTIDE | N | G | T | L | G | P | R | S | F | F | L | R | N |
| | | 3AA | | | | | G | P | R | | | | | | |
| | | 4AA | | | | L | G | P | R | | | | | | |
| | | 5AA | | | T | L | G | P | R | | | | | | |
| | | 6AA | | G | T | L | G | P | R | | | | | | |
| | | 7AA | N | G | T | L | G | P | R | | | | | | |

Furthermore, PAR-1 antagonist (1 μM) alone caused a significant 25% proliferation-inhibition in CNS-1 cells, wherein a combined treatment of the PAR-1 antagonist with NAPAP or TLCK significantly increased said inhibitory effect. The decreased proliferation of glioma cells in response to PAR-1 pathway modulation is a major finding, suggestive of the potential of PAR-1-based compounds as thrombin inhibitor for treating neuropathy and glioma, such as, GBM.

Figure 9:
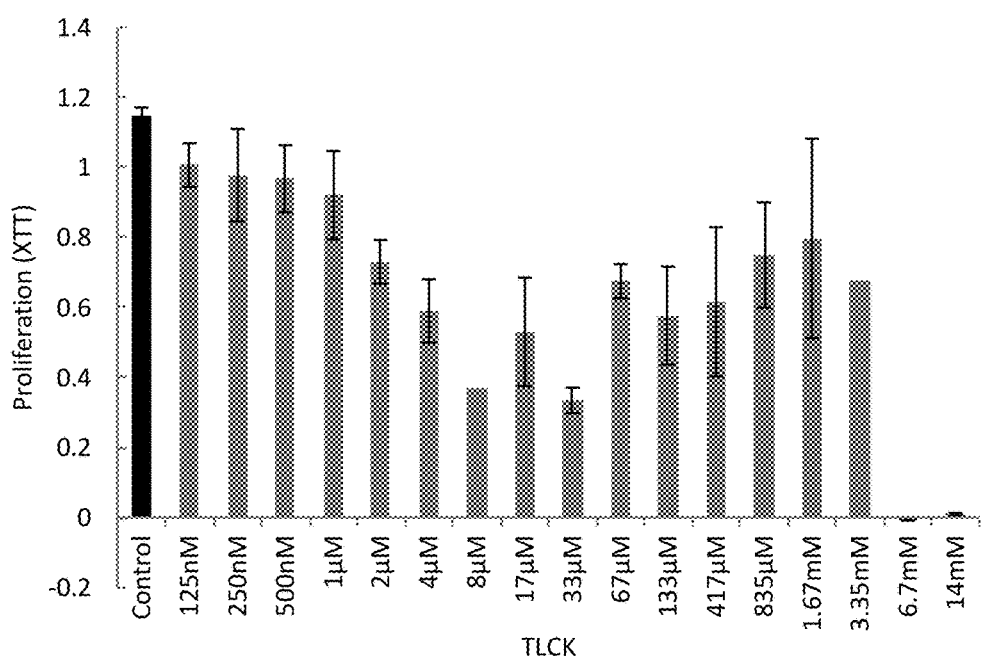
FIG. 9 exhibits proliferation of CNS-1 glioma cell-line upon dose-dependent treatment with TLCK (grey bars) compared to non-treated cells (black bar).
Figure 10:
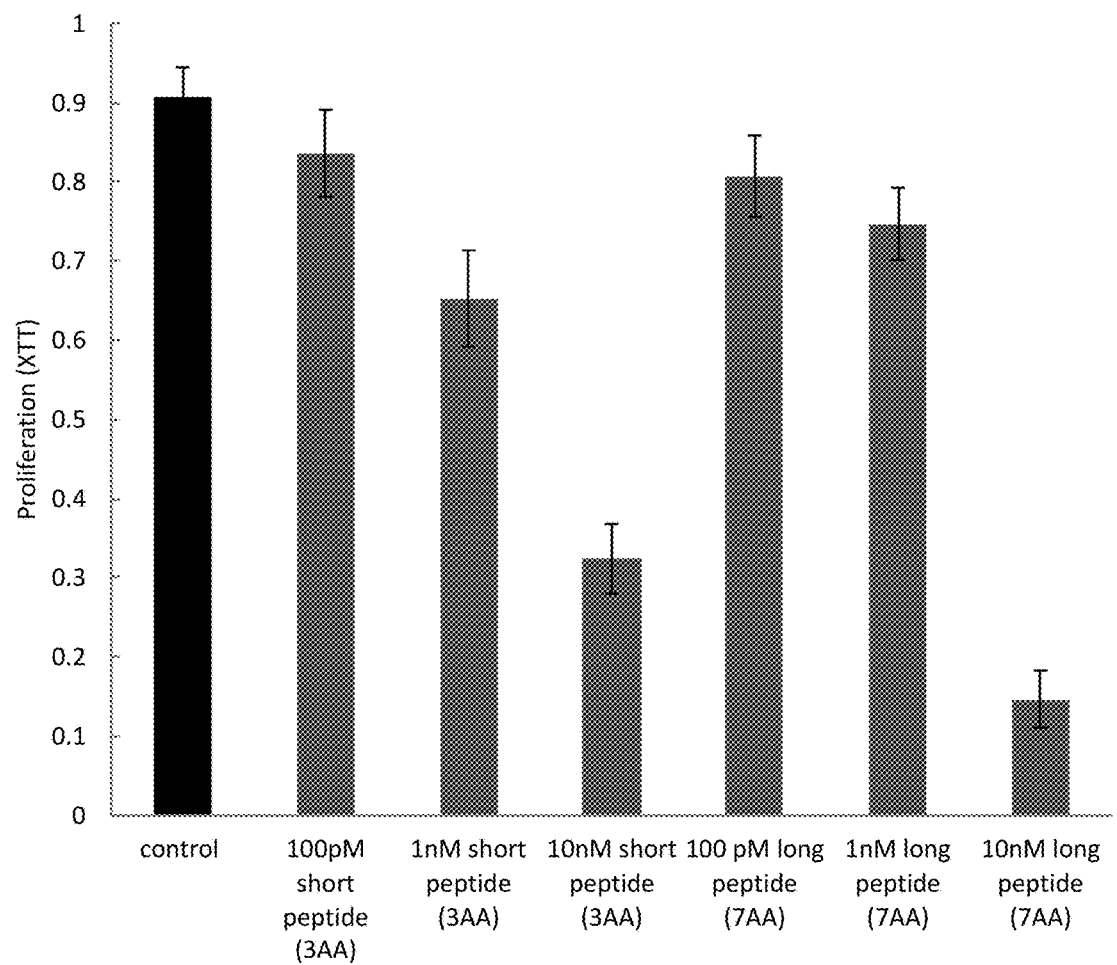
FIG. 10 presents the effect of the various doses of the peptide conjugates encompassing the peptide Asp-Pro-Arg (short peptide; 3AA) and the peptide set forth in SEQ ID NO: 4 (long peptide; 7AA) on proliferation of CNS-1 glioma cell-line (grey bars) relative to control (non-treated cells black bar).
Figure 11A:
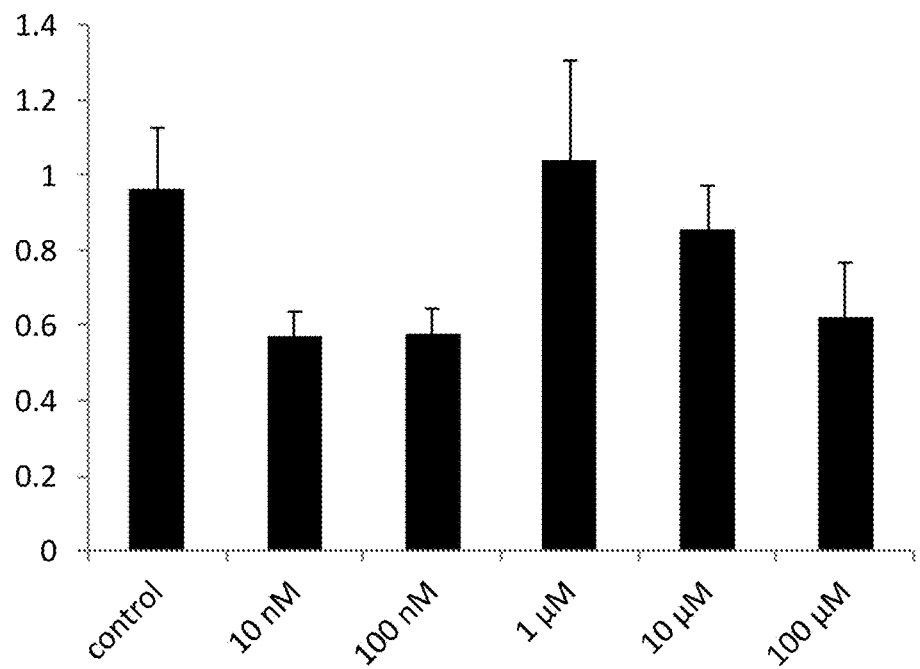
FIG. 11 presents dose-dependent inhibition of glioma proliferation by different concentrations of the peptide conjugates encompassing the peptide Asp-Pro-Arg and the peptides of SEQ ID NOs: 2-4 (11A-11D, respectively) after 48 h.
Figure 11B:
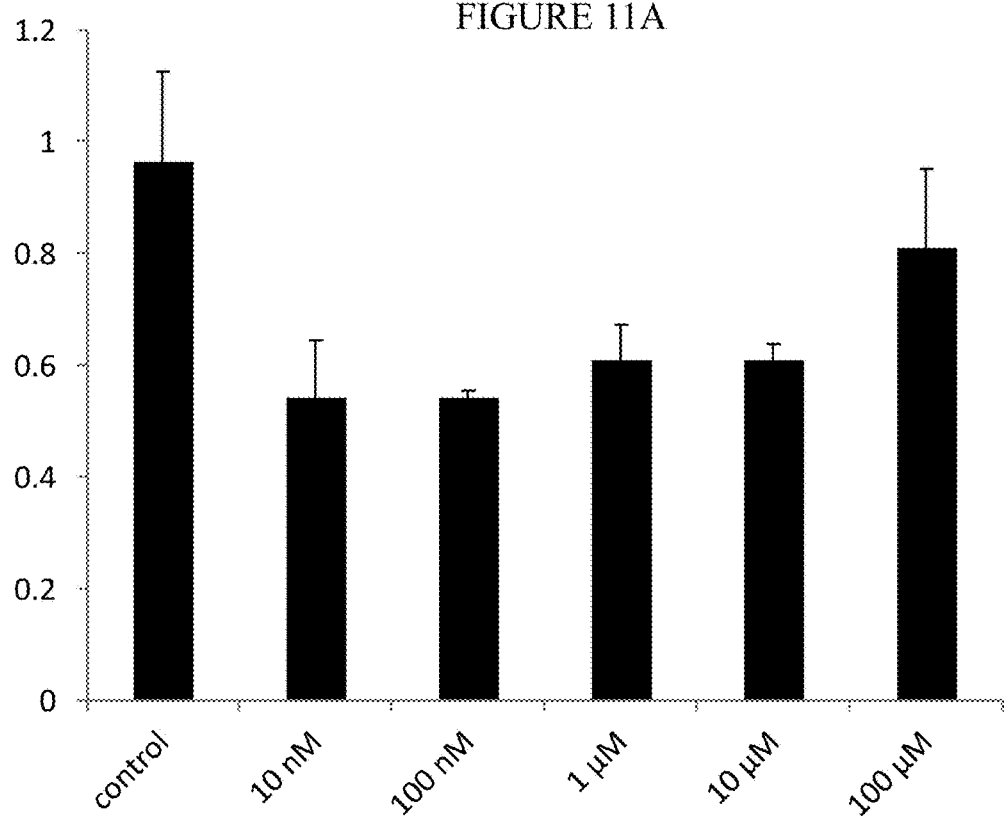
Figure 11C:
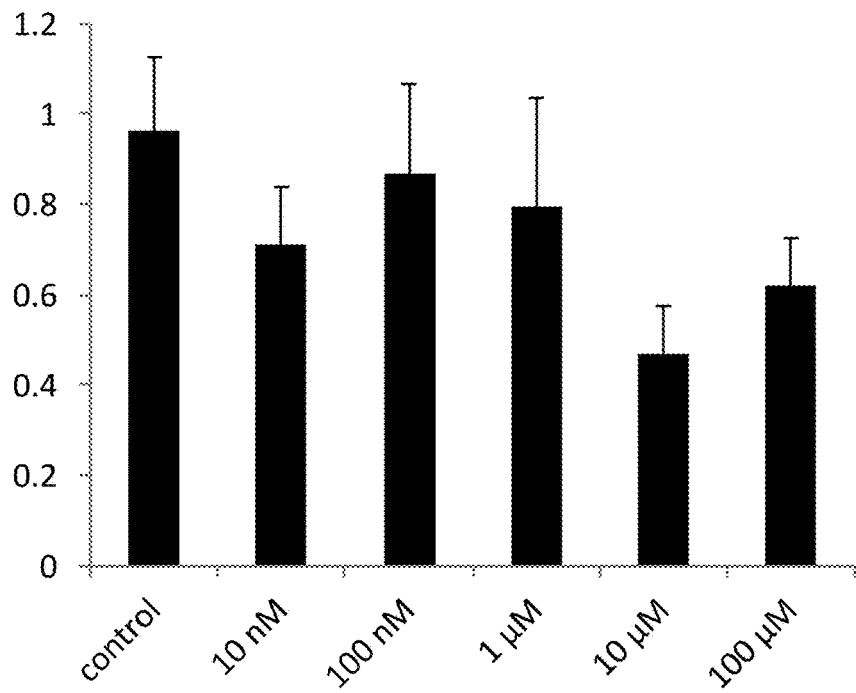
Figure 11D:
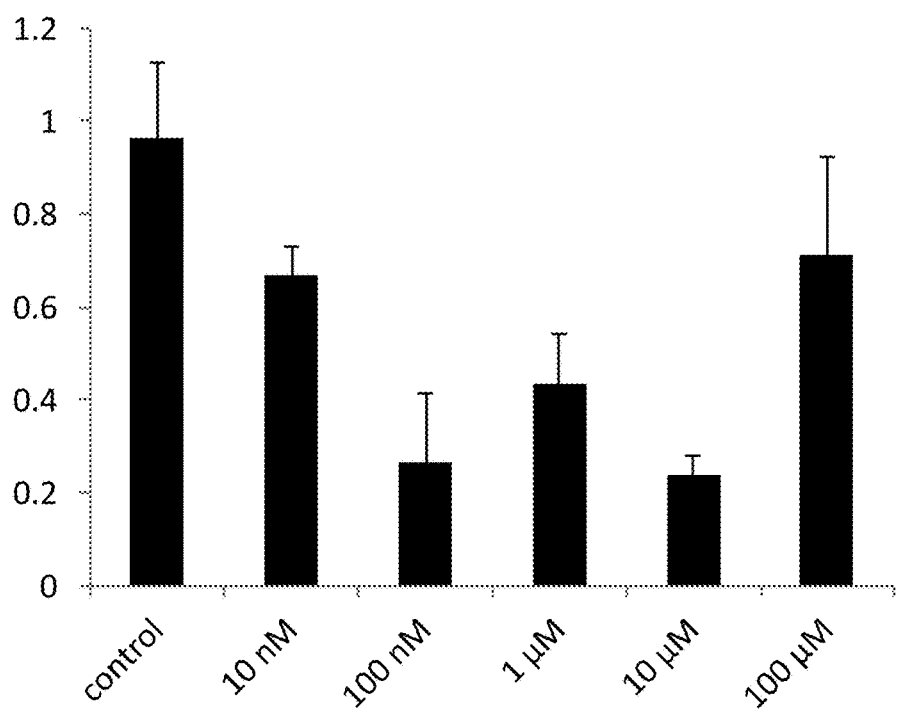
Figure 12A:
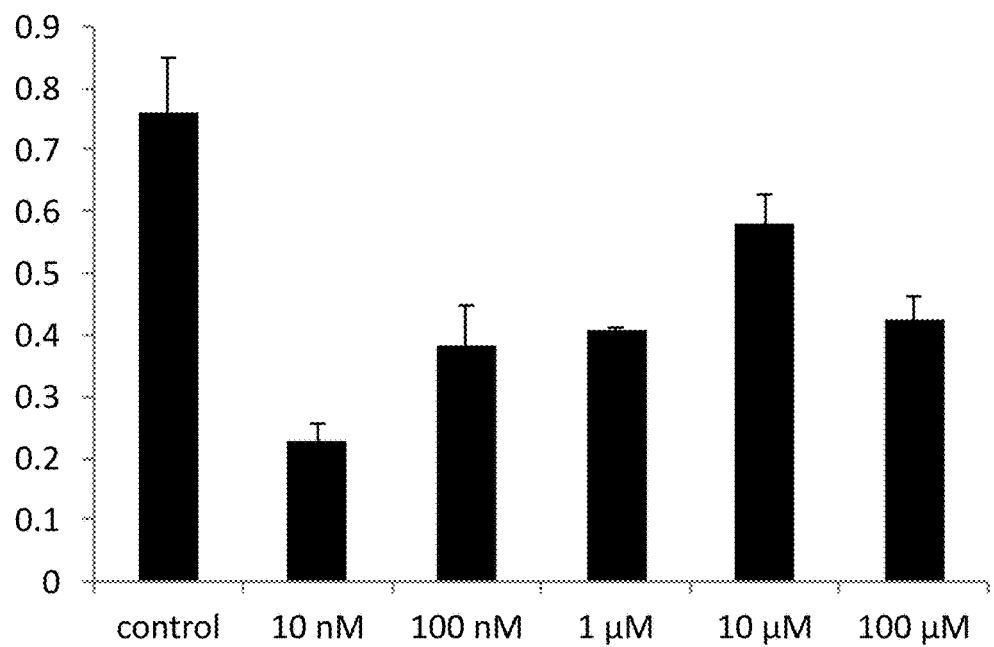
FIG. 12 presents dose-dependent inhibition of glioma proliferation by different concentrations of the peptide conjugates encompassing the peptide Asp-Pro-Arg and the peptides of SEQ ID NOs: 2-4 (12A-12D, respectively) after 72 h.
Figure 12B:
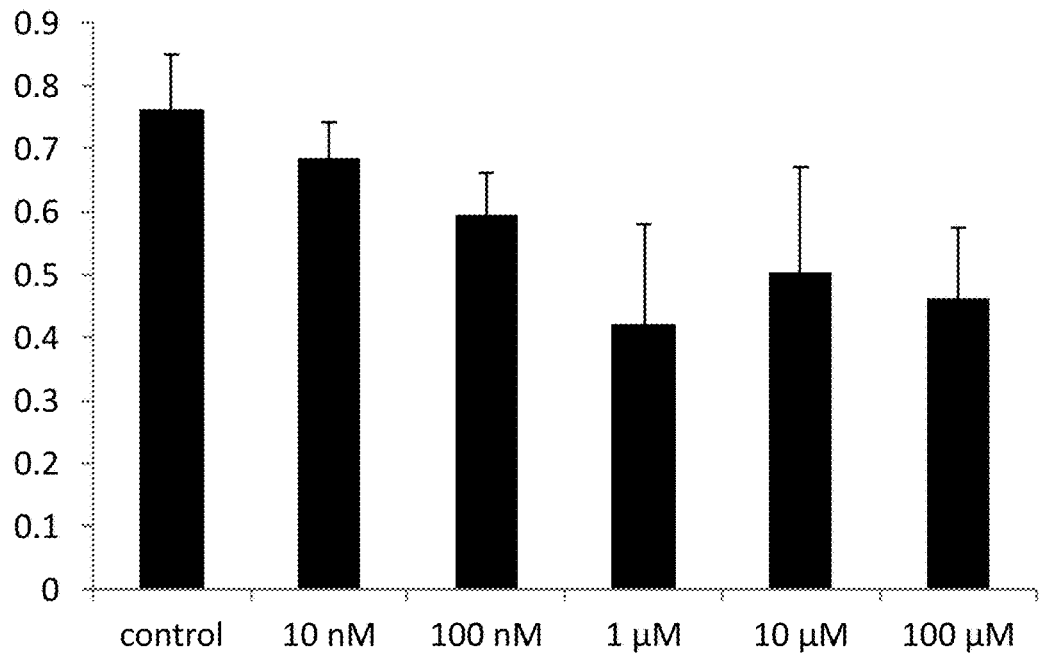
Figure 12C:
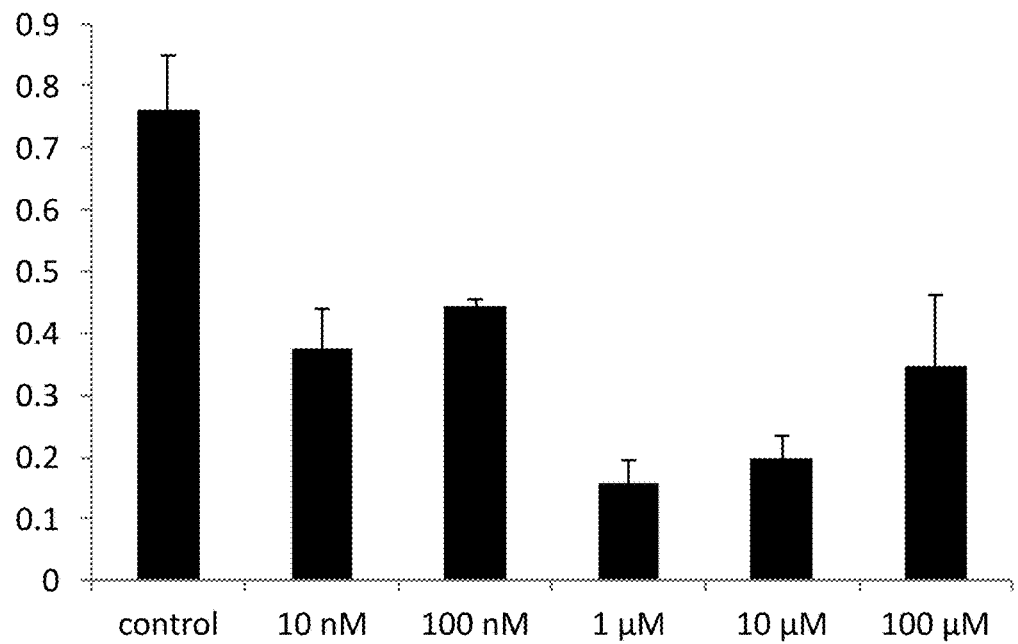
Figure 12D:
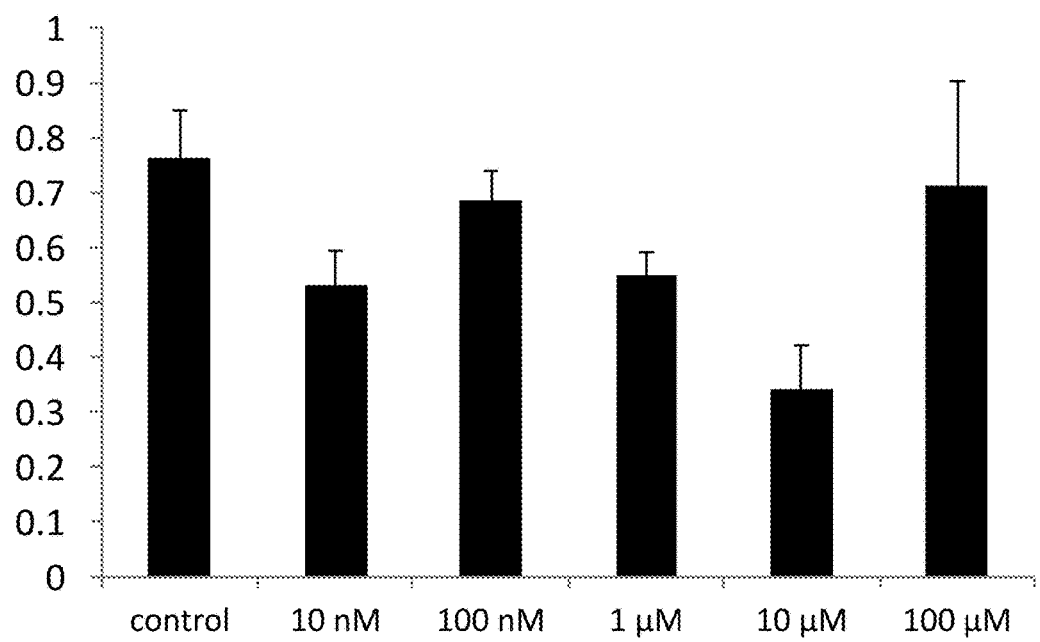

In another set of experiments, CNS-1 glioma cell-line was treated with increased doses of TLCK (125 nM to 14 mM), for 48 hours (FIG. 9; grey bars). Proliferation was measured by means of XTT in comparison to non-treated cells (control; black bar). High concentrations of TLCK (6.7 mM, 14 mM) caused cell death, and at the micro-molar range (8-33 μM) a significant proliferation-inhibition occurred. No significant proliferation-inhibition was seen between 1 μM to 125 nM It is therefore evident that the highly effective thrombin inhibitor TLCK decreased glioma-cell proliferation at relatively high concentrations (i.e. higher than 1 μM), with the downside of increased risk for hemorrhage. The new PAR-1-based conjugates provided by the present invention pro-concentrations of 100 pM, 1 nM and 10 nM, for 48 hours (FIG. 10). FIG. 10 provides the results of an XTT assay used for assessing cell proliferation. The results indicate that the short conjugate (3AA) caused significant inhibition of cell proliferation at 1 nM and higher inhibition at 10 nM, while the long conjugate (7AA) caused a significant inhibition at 10 nM, relative to untreated control (FIG. 10).

CNS-1 glioma cells were treated with increased concentrations of the peptide conjugates containing the peptide DPR or the peptides of SEQ ID NOs: 2-4 for 48 hours and for 72 hours (FIGS. 11 and 12, respectively). As seen in FIG. 11, a trend to reduced proliferation was observed in the samples treated with the peptide conjugates compared to controls at 48 hours. Significant inhibition, relative to untreated controls, was noted for 10 μM peptide conjugate encompassing the peptides 6AA and 7AA ($p<0.05$). At the 72 hour experiment (FIG. 12) significantly lower proliferation was found for all concentrations of the peptide conjugate containing the 6AA peptide compared to controls ($p<0.05$). This observation was most significant at concentrations of 1 and 10 micromolar ($p=0.002$ and $0.003$, respectively). Similar inhibitory effect was observed under treatment with the peptide conjugate that includes the 3AA peptide, at all tested concentrations, compared to controls (p<0.05). The results indicate that the inhibition of cell proliferation as exhibited by the peptide conjugates is significantly greater than cell proliferation of the control cells, namely, cells not incubated with any of the peptide conjugates. Moreover, the inhibitory effect exerted by the peptide conjugate was prominent even at concentrations as low as the range of micromolars and nanomolars.

Example 10. Proliferation Inhibition Relative to PAR-1 Inhibitory Activity

Figure 13:
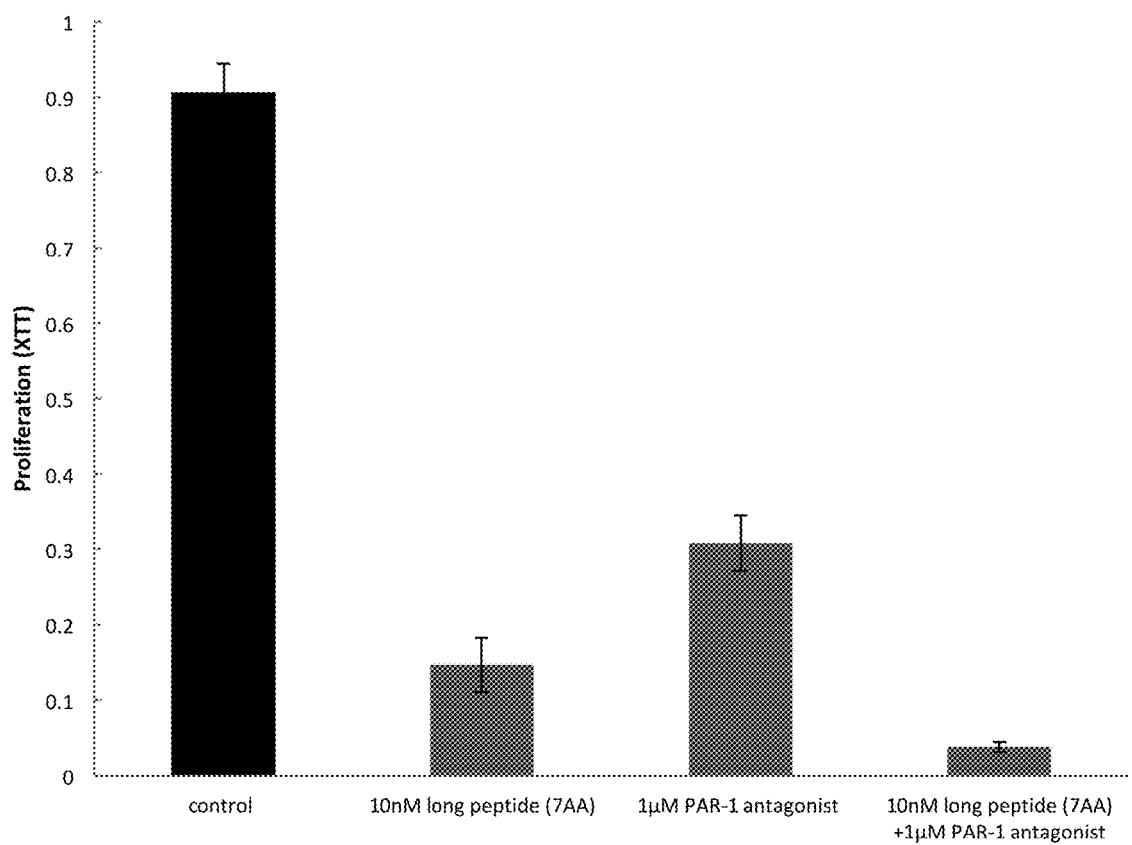
FIG. 13 presents the effect of the peptide conjugates encompassing the peptide set forth in SEQ ID NO: 4 (7AA) with or without PAR-1 antagonist (1 µM) on proliferation (XTT) of CNS-1 glioma cell-line (grey bars) compared to untreated cells (control; black bar).

The effect of the peptide conjugate alone, or in combination with PAR-1 antagonist, SCH79797, on cell proliferation was determined in comparison to untreated cells or cells treated with PAR-1 antagonist (FIG. 13). The results indicate that the peptide conjugate, as exemplified by a conjugate comprising the peptide set forth in SEQ ID NO:4, induces a greater inhibition on cell proliferation when applied alone or in combination with PAR-1 antagonist, compared to control (untreated cells) and even compared to PAR-1 antagonist alone.

Example 11. Anti-Thrombin-Activity Ex-Vivo

Figure 14A:
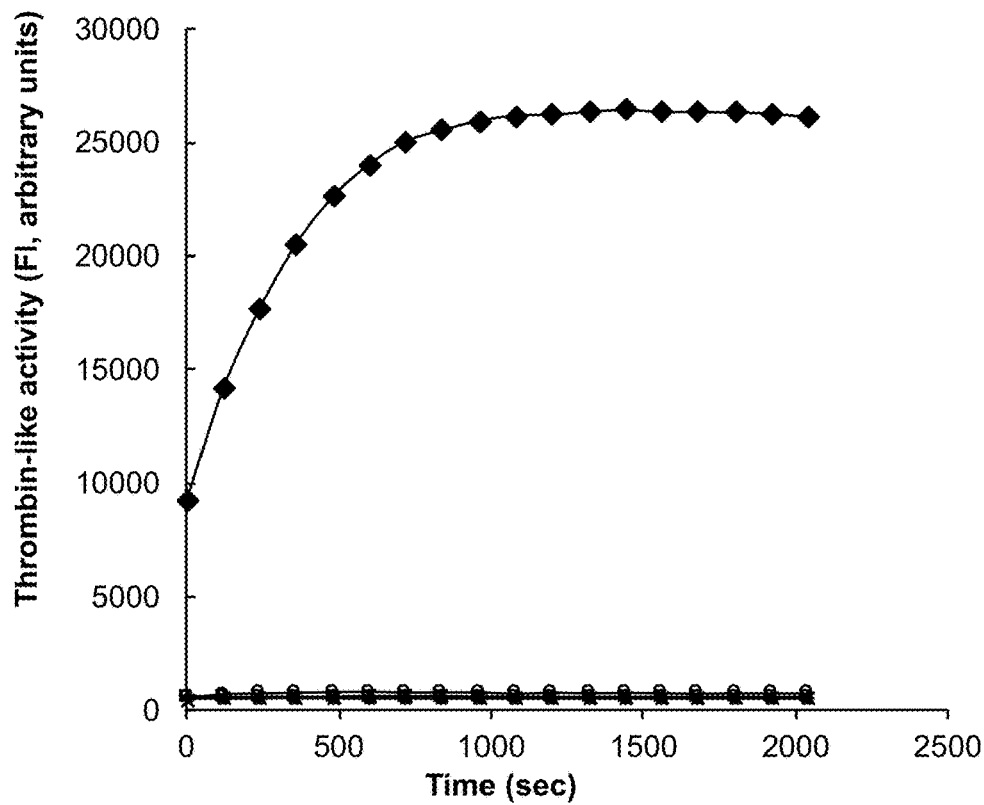
FIG. 14 presents thrombin-like activity in thrombin inhibition assay under various doses of the peptide conjugates (from 156 nanomolar to 1 mM to) encompassing the peptide Asp-Pro-Arg (3AA; A) and the peptide set forth in SEQ ID NO: 4 (7AA; B) relative to control (i.e. without the presence of an of the peptide conjugates (diamonds).
Figure 14B:
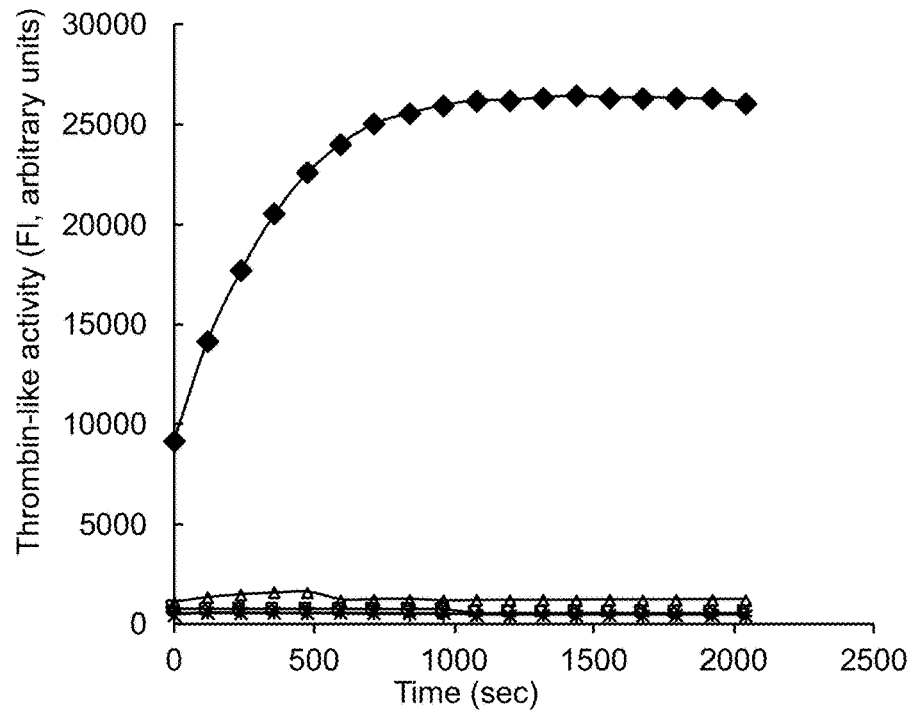

The activity of high concentrations (0.05 U/ml) of thrombin (FIGS. 14-14B; diamond) was measured after treatment with a wide dose-range of either the short conjugate (FIG. 14A, tosyl-DPR-CK, 3AA) or the long conjugate (FIG. 14B, tosyl-NATLDPR-CK, 7AA). Measurements were carried out in a thrombin inhibition non-cellular assay, which included a buffer, thrombin and a specific thrombin substrate which its cleavage indicates thrombin activity or inhibition. The conjugates concentrations applied were as follows: control (no treatment—0 nM; full diamond), 1 mM (vertical line), 50 µM (circle), 10 µM (cross), 1.25 µM (square) and 156 nM (triangle).

The data presented in FIGS. 14A-14B demonstrate that both peptide-conjugates have the ability to exert a complete inhibition of thrombin activity at a wide range of concentration, ranging from as high as 1 mM to as low as 156 nM.

Figure 15:
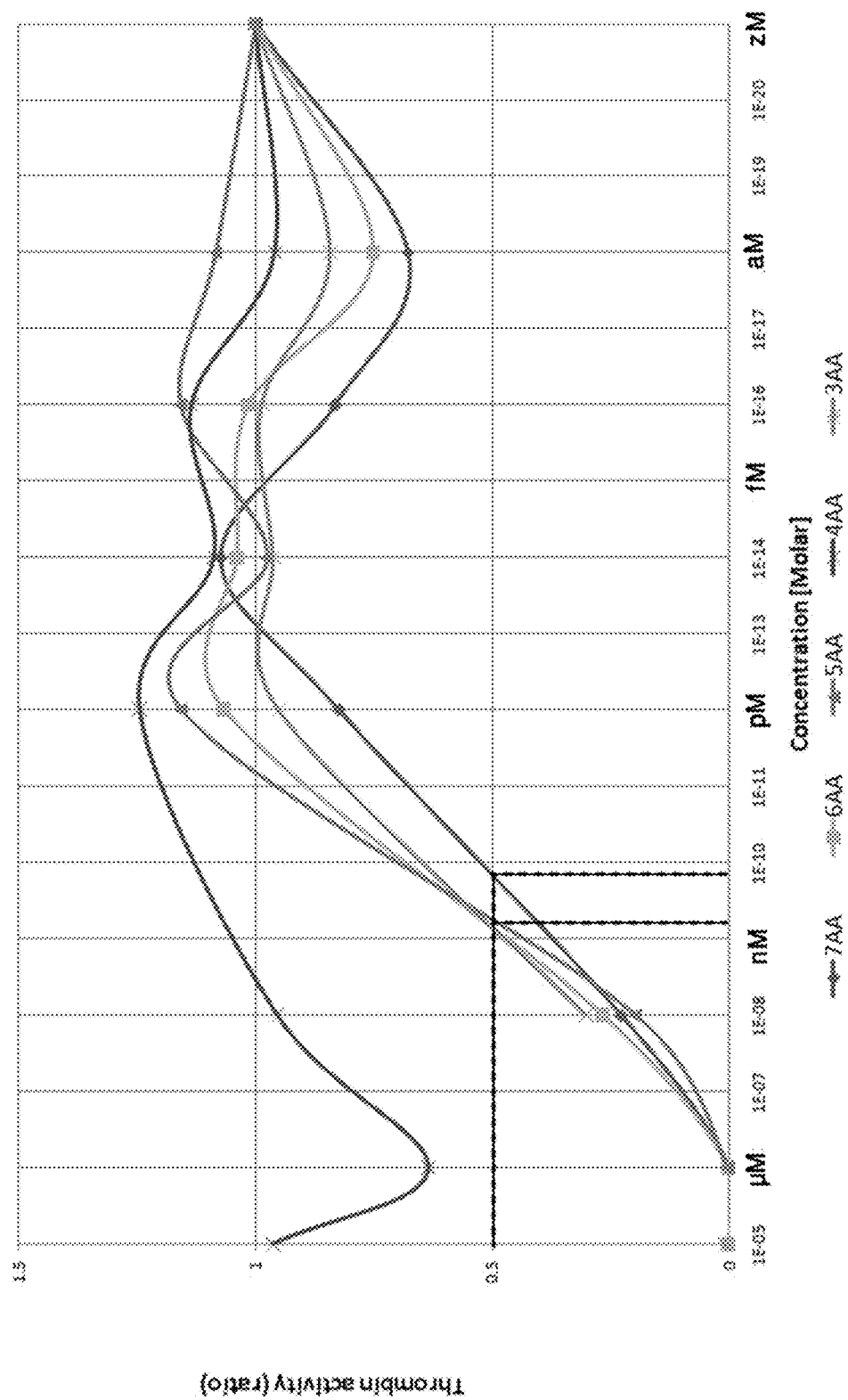
FIG. 15 presents thrombin activity (ratio) performed in a thrombin activity assay (non-cellular) under different concentrations of the peptide conjugates encompassing the peptide Asp-Pro-Arg (3AA; x, grey line) or the peptides set forth in SEQ ID NO: 1 (4AA; x, dark line); SEQ ID NO: 2 (5AA, triangle, dark line); SEQ ID NO: 3 (6AA; square, grey line) and SEQ ID NO: 4 (7AA; diamond, dark line).

FIG. 15 presents thrombin activity in the presence of peptide conjugates containing the peptide DPR (also termed 3AA; FIG. 15: x symbols on grey line) or the peptides set forth in SEQ ID NOs: 1-4 (also termed 4AA-7AA, respectively; FIG. 15: 4AA-x symbols on dark line, 5AA-triangles, 6AA-squares, 7AA-diamonds) determined in a non-cellular system as described above. The corresponding IC50 of peptide conjugates are listed in Table 3 below. These results demonstrate the efficacy of the peptide conjugates in inhibiting bovine serum thrombin.

TABLE 3

IC50 of the peptide conjugates

| IC50 | Peptide encompassed in the conjugate (SEQ ID NO.) |
|---|---|
| 700 pM | 3AA |
| — | §4AA (1) |
| 700 pM | 5AA (2) |
| 700 pM | 6AA (3) |
| 100 pM | 7AA (4) |

§Results were inconsistent

Example 12. Anti-Thrombin-Activity in CNS-1 Cells

Figure 16:
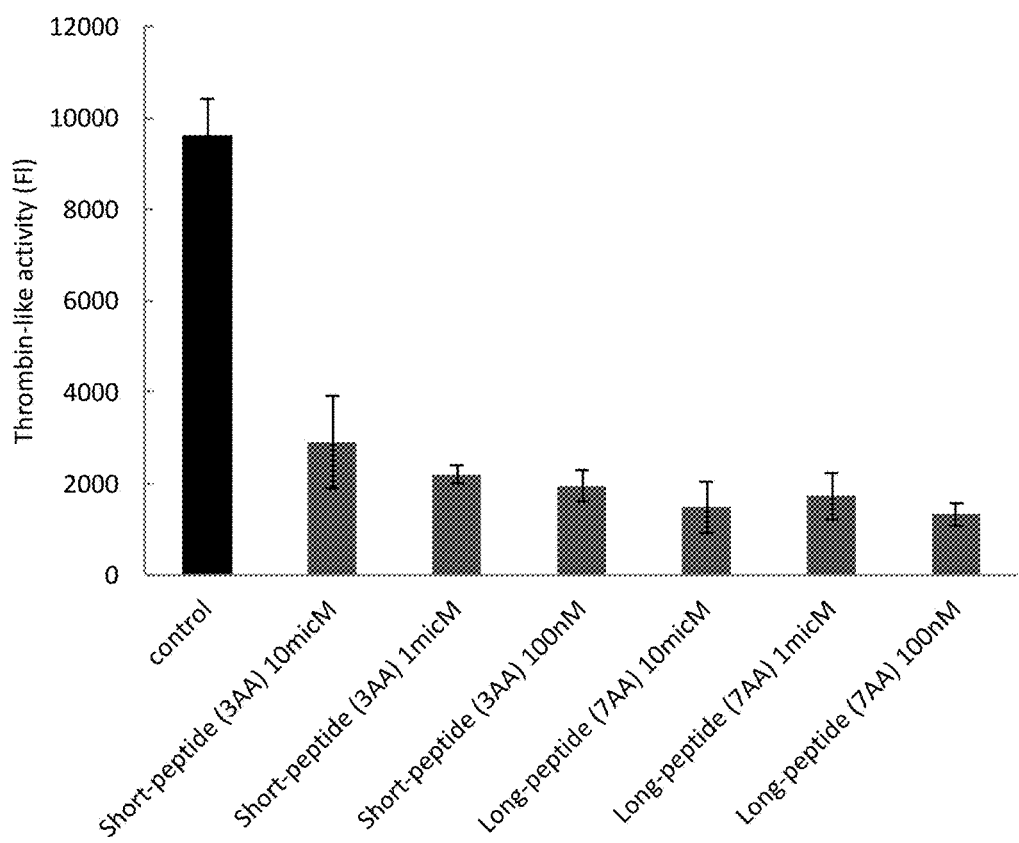
FIG. 16 presents the effect of the various doses of the peptide conjugates encompassing the peptide Asp-Pro-Arg (3AA) and the peptide set forth SEQ ID NO: 4 (7AA) on thrombin-like activity in CNS-1 glioma cell-line (grey bars) compared to untreated cells (control; black bar).

The thrombin-like activity of CNS-1 cells was initially measured in control cells and in cells treated with (i) the short peptide conjugate (tosyl-DPR-CK, corresponding to a conjugate that includes the peptide termed 3AA) or (ii) the long conjugate (tosyl-NATLDPR-CK, corresponding to a conjugate that includes the peptide termed 7AA (SEQ ID No. 4)) at high (10 mM) and low (100 nM) concentrations (FIG. 16).

At all range of concentrations, the peptide-conjugates induced a significant inhibition of thrombin-like activity generated by CNS-1 glioma cells.

Figure 17:
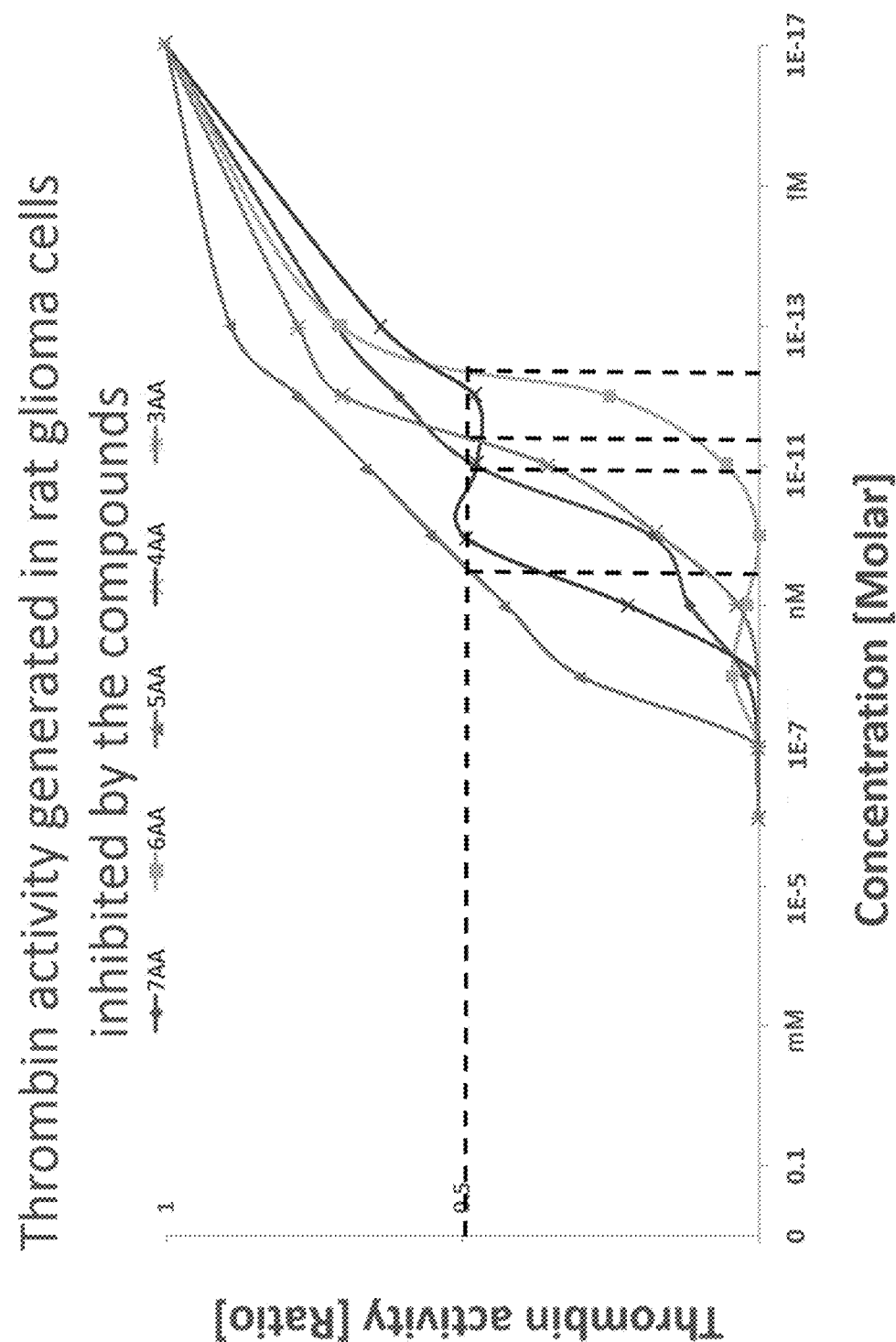
FIG. 17 presents thrombin activity (ratio) generated by rat glioma cells inhibited by different concentrations of the peptide conjugates encompassing the peptide Asp-Pro-Arg (3AA; asterisk) or the peptides set forth in SEQ ID NO: 1 (4AA; x); SEQ ID NO: 2 (5AA; triangle); SEQ ID NO: 3 (6AA; square) and SEQ ID NO: 4 (7AA; diamond).

FIG. 17 presents thrombin activity in the presence of peptide conjugates containing the peptide DPR (also termed 3AA; FIG. 17: asterisk) or the peptides set forth in SEQ ID NOs: 1-4 (also termed 4AA-7AA, respectively; FIG. 17: 4AA-x, 5AA-triangle, 6AA-square, 7AA-diamond) determined in rat glioma cells as described above. The corresponding IC50 of peptide conjugates are listed in Table 4 below:

TABLE 4

IC50 of the peptide conjugates in rat glioma cells

| IC50 | Peptide encompassed in the conjugate (SEQ ID NO.) |
|---|---|
| 7 pM | 3AA |
| — | 4AA (1) |
| 700 pM | 5AA (2) |
| 700 fM | 6AA (3) |
| 10 pM | 7AA (4) |

Example 13. Plasma Concentrations of the Conjugates In-Vivo

The concentrations of the peptide conjugates in the plasma of animals treated therewith was evaluated by a unique method that was based on the ability of the peptide conjugates to inhibit thrombin activity. Data was obtained for conjugate peptides comprising the peptide DPR and the peptides set forth in SEQ ID NO: 2; SEQ ID NO: 3; and SEQ ID NO: 4 (FIGS. 18A-18D, respectively). The essay initiated by obtaining blood samples from animals which received the peptide conjugates (100 microliter containing 2 micromolar, i.p.). The blood samples, after being maintained in citrate buffered sample tubes, were subjected to centrifugation for plasma separation. Samples were then filtered through a membrane with a 10 kD molecular weight cutoff which excluded all blood coagulation factors (by addition of calcium to neutralize the anticoagulation effect of the citrate buffer). Coagulation factor-free plasma samples were then applied to the thrombin activity assay.

Figure 18A:
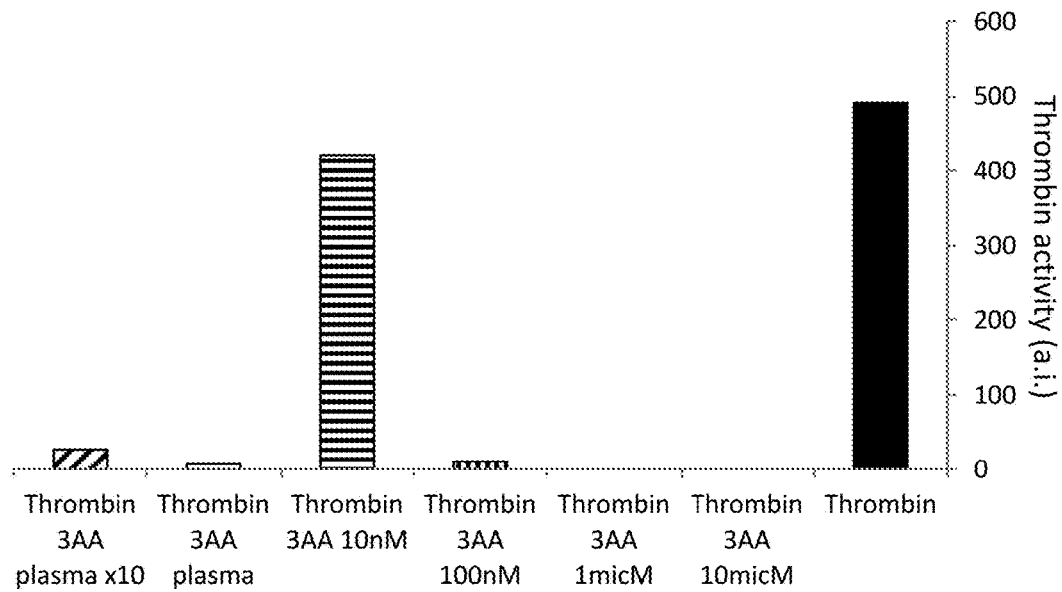
FIG. 18 presents thrombin activity in plasma samples after addition of the peptide conjugates encompassing the peptide Asp-Pro-Arg (A) or the peptides set forth in SEQ ID NO: 2 (B); SEQ ID NO: 3 (C); and SEQ ID NO: 4 (D).
Figure 18B:
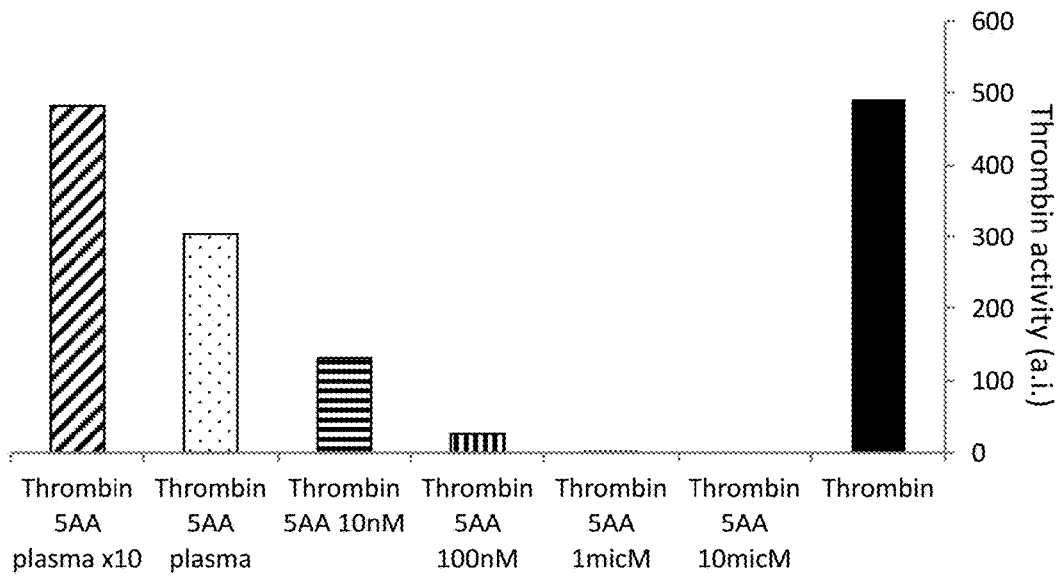
Figure 18C:
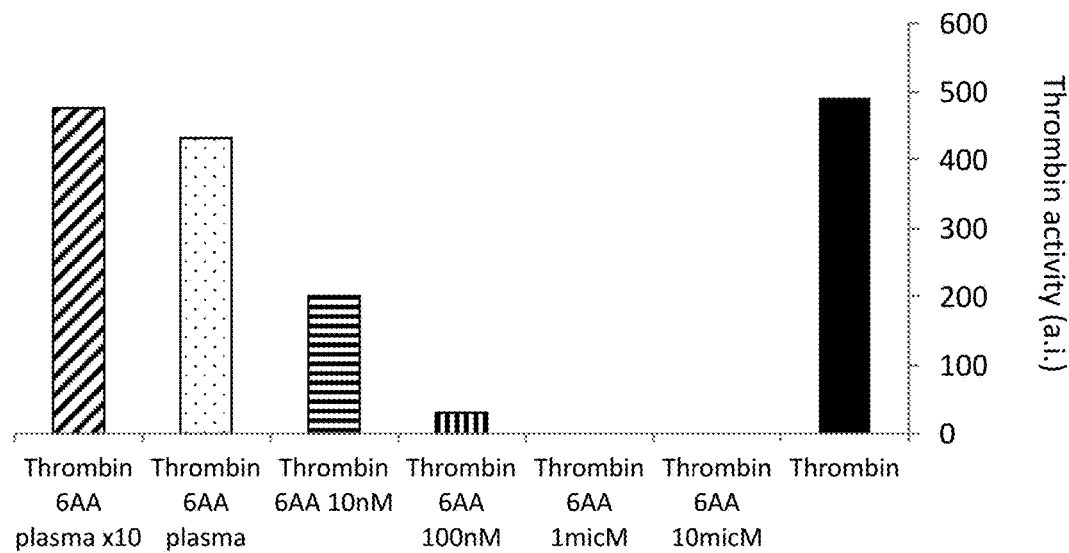
Figure 18D:
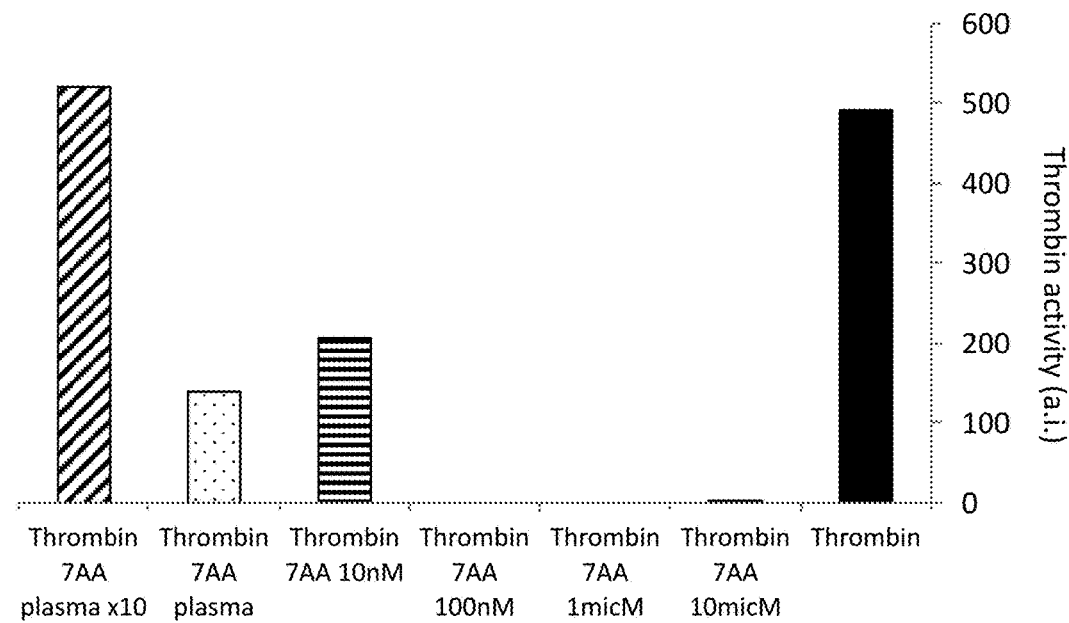

The resulting thrombin activities in each plasma sample either diluted (×10) or as is were given in arbitrary units (FIGS. 18-18D, diagonal shading and dotted bars, respectively). However, the actual concentration were deduced by comparing the activities to calibrated activities generated with known concentrations of the conjugate peptides. The calibration data included the following thrombin activities: activity in a sample of thrombin in the absence of plasma and conjugates (black bars, FIGS. 18A-18D); and activity in four samples of thrombin and known concentrations of the peptide conjugates (10 nM, 100 nM, 1 micromolar and 10 micromolar; bars $2^{nd}$ to 5th from right in FIGS. 18A-18D). The comparison to calibration data indicates that an i.p. injection of 100 μl containing 2 micromolar of each peptide conjugate resulted in a serum concentration of about 1 μM for the peptide conjugate containing the 3AA peptide, less than 10 nM for the peptide conjugates containing the 5AA and 6AA peptides, and about 10 nM for the peptide conjugates containing the 7AA peptide. The results also suggest that the assay used herein is suitable for measuring the levels of the peptide conjugate and to identify significant differences in their distribution and stability in vivo.

Example 14. The Effect of the Peptide Conjugates on Blood Coagulation

Tables 5-9 below represent the effect of the peptide conjugates comprising the peptide DPR and the peptides set forth in SEQ ID NOs: 1-4 on the following standard blood coagulation tests: Prothrombin time (PT, Table 5), activated Partial thromboplastin time (aPTT, Table 6), thrombin time (TT, Table 7), Factor Xa activity (Fxa; Table 8) and Protein C activity (Table 9) using standard hematology lab tests. For each test the most potent peptide conjugate to least potent were scored from (1) to (5). In the PT and PTT tests only very high concentrations (100 μM) of the peptide conjugate significantly affected coagulation. Since a selection towards the conjugates least likely to affect coagulation systemically was applied, the peptide conjugate having the 3AA peptide stood out as having significantly more deleterious effects on coagulation. The most sensitive test for verifying the effect of the peptide conjugates in general was TT. Without being bound to any theory or mechanism, it is assumed that the TT test was most sensitive because it supports the mechanism of action of the peptide conjugates as direct thrombin inhibitors. Thus, the TT test indicates that the conjugates are useful inhibitors. Moreover, the results suggest that the peptide conjugate exert their therapeutic activity without interfering with coagulation. This is an outstanding benefit, as the current thrombin inhibitors cause internal bleeding.

TABLE 5

Prothrombin time test

| PT | 0 | 10 nM | 1 μM | 100 μM (Potency) |
|---|---|---|---|---|
| 3AA | 11.5 | 11.5 | 12.3 | FAILED (1) |
| 4AA | 11.5 | 11.5 | 11.4 | 12.7 (5) |
| 5AA | 11.5 | 12.1 | 11.5 | 14.5 (4) |
| 6AA | 11.5 | 11.5 | 11.4 | 16.5 (3) |
| 7AA | 11.5 | 11.5 | 11.2 | 17.4 (2) |

TABLE 6

Activated Partial thromboplastin time test

| aPTT | 0 | 10 nM | 1 μM | 100 μM (Potency) |
|---|---|---|---|---|
| 3AA | 30.5 | 30 | 38.1 | 150 (1) |
| 4AA | 30.5 | 30.8 | 30.9 | 42.6 (5) |
| 5AA | 30.5 | 30.1 | 30.5 | 63.9 (4) |
| 6AA | 30.5 | 30 | 30.6 | 67.6 (3) |
| 7AA | 30.5 | 29.9 | 30.7 | 85.2 (2) |

TABLE 7

Thrombin time test

| TT | 0 | 10 nM | 1 μM (Potency) | 100 μM |
|---|---|---|---|---|
| 3AA | 13.4 | 14.1 | >80 (1) | >80 |
| 4AA | 13.4 | 13.5 | 14.6 (5) | >80 |
| 5AA | 13.4 | 13.8 | 17.8 (4) | >80 |
| 6AA | 13.4 | 13.9 | 18.5 (3) | >80 |
| 7AA | 13.4 | 13.5 | 24.1 (2) | >80 |

TABLE 8

Factor Xa activity test

| Fxa | 0 | 1 μM | 100 μM (Potency) |
|---|---|---|---|
| 3AA | 0.11 | 0.21 | FAILED (1) |
| 4AA | 0.11 | | 0.11 (5) |
| 5AA | 0.11 | | 0.13 (4) |
| 6AA | 0.11 | | 0.36 (3) |
| 7AA | 0.11 | | 0.43 (2) |

TABLE 9

Protein C activity test

| aPC | 0 | 1 μM | 100 μM (Potency) |
|---|---|---|---|
| 3AA | 109 | 107 | FAILED (1) |
| 4AA | 109 | 108 | 66 (5) |
| 5AA | 109 | 109 | 20 (3) |
| 6AA | 109 | 108 | 11 (2) |
| 7AA | 109 | 110 | 25 (4) |

Example 15. Conduction Velocities in the Sciatic Nerve of an Animal Model for Diabetic Neuropathy Streptozotocyn (STZ) was dissolved in citrate buffer pH 4.5 and a single dose of STZ was administered IP (140 mg/kg) to 12 weeks BALB/c mice. Hyperglycemia (over 300 mg/dl blood glucose) was observed in 90% of the mice in 3 repeated measurements within a week from the STZ injection. Mice developed diabetic neuropathy developed within 4 weeks after the induction of diabetes. Mice were treated daily with sham (STZ), or with the a peptide conjugate as the active drug, exemplified by the conjugate T5AACK (i.e. a conjugate comprising the peptide set forth in SEQ ID NO:2) injected in 100 microliter volume containing the following doses: 10 nM, 100 nM and 1 micromolar. A group of normal mice without diabetes served as controls.

Figure 19:
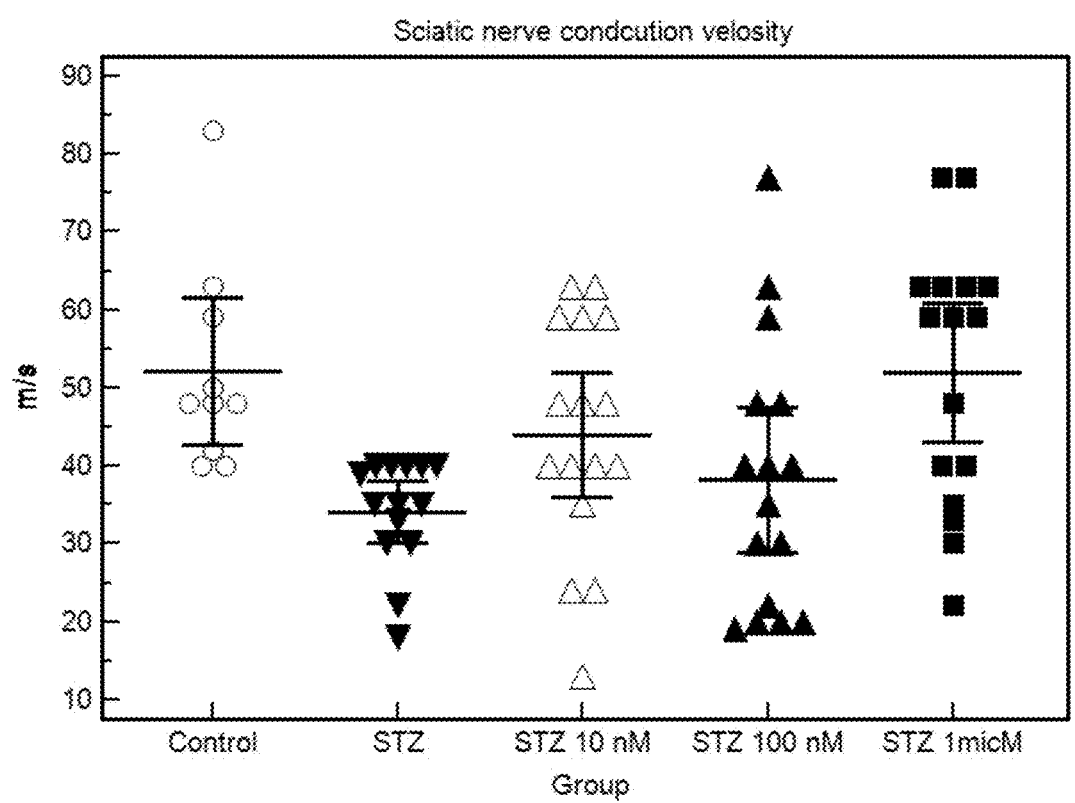
FIG. 19 presents sciatic nerve conduction velocity (m/s) in a Diabetes melitus mice model (induced by streptozotocin (STZ) injection) untreated (STZ) or treated with T5AACK (a peptide conjugate encompassing the peptide 5AA (SEQ ID NO: 2) nested between tosyl and CK) at different concentrations and compared to normal mice without diabetes (Control).

Conduction velocities in the sciatic nerves of the mice were assessed by standard electrophysiology nerve conduction methods by a blind assessor (FIG. 19). T-test analysis of indicated that the effect of the peptide conjugate T5AACK relative to sham treated mice was highly significant: 1 micromolar, p=0.00046 and 10 nM, p=0.016.

Thus, the conduction velocity of the sciatic nerve in diabetic mice treated with the peptide conjugate resembled that of normal, health mice.

Example 16. Tumor Size and Edema in GBM Animal Model

The therapeutic effect of the peptide conjugate was determined in-vivo in an animal (rat) model of GBM using a peptide conjugate that includes the 6AA peptide (SEQ ID NO: 3).

Cells ($0.5 \times 10^6$ cells) from a highly malignant cell line of rat Glioblastoma multiforme (GBM) were injected by stereotactic methods into the parietal cortex of rats. Five (5) days later the brain of these rats were examined by MM and the tumors scored on a scale of 1-3 (1-small size tumor, 2-middle size tumor, 3-large size tumor) and for ventricular localization of the tumor. A catheter was placed in the brain tumor and attached to an osmotic pump (Alzet) releasing 1 μl/h for 7 days of one of the following three (3) treatments: saline (n=13), 6AA 2 μM (n=14) and 6AA 20 μM (n=14). Following seven (7) days of treatments an MRI was performed and the size of the tumor and edema surrounding the tumor was analyzed by standard ROI manual techniques for each rat and summarized for all three groups of treatment (1) control; (2) treatment with 2 μM of a peptide conjugate comprising the peptide termed 6AA (SEQ ID NO: 3); and (3) treatment with 20 μM of a peptide conjugate comprising the peptide termed 6AA (SEQ ID NO: 3).

Figure 21:
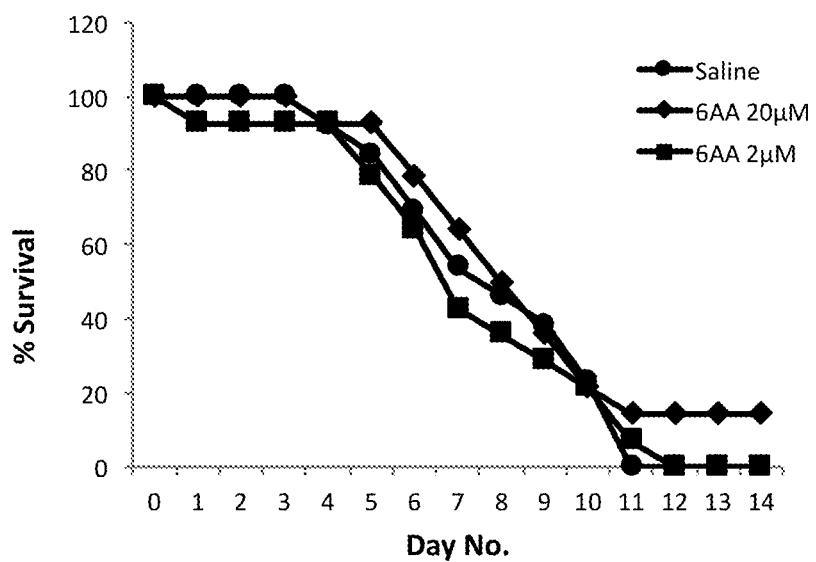
FIG. 21 presents the percentage survival of rats in the following treatment groups: control (saline; circle), 2 µM of a peptide conjugate comprising the peptide termed 6AA (SEQ ID NO: 3; square), and 20 µM of a peptide conjugate comprising the peptide termed 6AA (SEQ ID NO: 3; diamond).

In order to account for the unequal distribution of initial tumor size, tumor and edema analyses were performed on rats with grade 1 and 2 tumors in the initial Mill (n=7, 6 and 5 for the saline, low and high treatment groups, respectively). The results for the changes in tumor size (i.e. the size obtained in second (post treatment) MM minus the size in initial (baseline, t=0) Mill) and similarly change in edema are presented in FIGS. 20 and 21, respectively. As shown by FIGS. 20 and 21, high dose treatment reduced tumor size to half of the original size (p=0.030, t-test). A similar trend was observed for the low dose group. In addition, both doses caused reduction in the edema surrounding the tumors.

Survival was registered daily (FIG. 21). None of the 3 rats with severe initial tumors (grade 3 or ventricular) survived to perform the second Mill, compared to all 3 severe tumor rats in the high dose (6AA 20 μM) treatment group and 1 out of 3 in the low dose group (p=0.05 for the high dose group compared to controls and p=0.024 for the high dose group compared to the other 2). As shown in FIG. 21, there was a clear trend to increased survival in the high dose 20 μM group and this group included 2 mice with exceptionally long survival which is borderline in significance to no survival in the other groups (p=0.055 by Fisher's exact test).

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A peptide conjugate comprising:
   an alpha-amino protecting moiety,
   a peptide consisting of the amino acid sequence selected from the group of Asp-Pro-Arg and SEQ ID NOs: 1-17, and
   a protease-disabling moiety,
   wherein the peptide is bound to the alpha-amino protecting moiety and to the protease-disabling moiety, wherein the protease-disabling moiety is chloromethylketone or derivatives thereof and wherein the alpha-amino protecting moiety is tosyl or derivatives thereof.

2. The peptide conjugate of claim 1, wherein the alpha-amino protecting moiety is bound to the N'-terminus amino acid sequence of the peptide directly or via a linker.

3. The peptide conjugate of claim 1, wherein the protease-disabling moiety is bound to the C'-terminus amino acid sequence of the peptide directly or via a linker.

4. A pharmaceutical composition comprising the peptide conjugate of claim 1 and a pharmaceutically acceptable carrier.

5. The pharmaceutical composition of claim 4, further comprising trichloroacetate.

6. The pharmaceutical composition of claim 4, further comprising a PAR-1 antagonist.

7. A method of treating a disease or disorder associated with excessive protease receptor activity in a subject in need of such treatment, comprising administering to said patient a therapeutically effective amount of a pharmaceutical composition comprising a peptide conjugate and a pharmaceutically acceptable carrier, said peptide conjugate comprising an alpha-amino protecting moiety, said peptide consisting of the amino acid sequence selected from the group of Asp-Pro-Arg and SEQ ID NOs: 1-17, and a protease-disabling moiety, wherein the peptide is bound to the alpha-amino protecting moiety and to the protease-disabling moiety, wherein the protease-disabling moiety is chloromethylketone or derivatives thereof and wherein the alpha-amino protecting moiety is tosyl or derivatives thereof.

8. The method of claim 7, wherein the protease receptor is PAR-1.

9. The method of claim 7, wherein the subject in need thereof is a subject afflicted with said disease or disorder or a subject susceptible to said disease or disorder.

10. The method of claim 7, wherein said disease or disorder is selected from the group consisting of neuroinflammation, neuroinflammatory diseases or disorders, neurodegenerative disease or disorder, neuropathy and diabetes-related neuropathy.

11. The method of claim 7, further comprising administering a second therapeutic agent in combination with said peptide conjugate.

12. The method of claim 11, wherein the second therapeutic agent is a PAR-1 antagonist.

13. A method for inducing a reduction in thrombin activity in a subject in need of such treatment, comprising administering to said subject a therapeutically effective amount of a pharmaceutical composition comprising a peptide conjugate and a pharmaceutically acceptable carrier, said peptide conjugate comprising an alpha-amino protecting moiety, the peptide consisting of the amino acid sequence selected from the group of Asp-Pro-Arg and SEQ ID NOs: 1-17, and a protease-disabling moiety, wherein the peptide is bound to the alpha-amino protecting moiety and to the protease-disabling moiety, wherein the protease-disabling moiety is chloromethylketone or derivatives thereof and wherein the alpha-amino protecting moiety is tosyl or derivatives thereof.

14. The peptide conjugate of claim 1, wherein the peptide is consisting of Asp-Pro-Arg.

15. The peptide conjugate of claim 1, wherein the peptide is consisting of SEQ ID NO: 5.

* * * * *